(12) United States Patent
Hagberg et al.

(10) Patent No.: US 8,710,243 B2
(45) Date of Patent: Apr. 29, 2014

(54) ESTROGEN RECEPTOR LIGANDS

(75) Inventors: Lars Hagberg, Stockholm (SE); Sandra Gordon, Mariefred (SE); Aiping Cheng, Huddinge (SE); Theresa Apelqvist, Grödinge (SE); Patrik Rhönnstad, Kungsör (SE); Mattias Wennerstål, Hägersten (SE)

(73) Assignee: Karo Bio AB, Huddinge (SE)

( * ) Notice: Subject to any disclaimer, the term of this patent is extended or adjusted under 35 U.S.C. 154(b) by 0 days.

(21) Appl. No.: 13/500,471

(22) PCT Filed: Oct. 6, 2010

(86) PCT No.: PCT/EP2010/064939
§ 371 (c)(1),
(2), (4) Date: Apr. 5, 2012

(87) PCT Pub. No.: WO2011/042473
PCT Pub. Date: Apr. 14, 2011

(65) Prior Publication Data
US 2012/0202861 A1    Aug. 9, 2012

(30) Foreign Application Priority Data

Oct. 7, 2009 (GB) .................................. 0917575.3
Mar. 16, 2010 (GB) .................................. 1004377.6

(51) Int. Cl.
*C07D 209/12* (2006.01)

(52) U.S. Cl.
USPC ........................................................ 548/511

(58) Field of Classification Search
USPC ........................................................ 548/469
See application file for complete search history.

(56) References Cited

U.S. PATENT DOCUMENTS

2003/0220377 A1   11/2003   Chesworth

FOREIGN PATENT DOCUMENTS

| EP | 1779848 | 5/2007 |
| JP | 2001122855 | 5/2001 |
| WO | 2005105213 | 11/2005 |
| WO | 2007087488 | 8/2007 |
| WO | 2008043567 | 4/2008 |
| WO | 2009012954 | 1/2009 |
| WO | 2009124968 | 10/2009 |
| WO | 2009127686 | 10/2009 |
| WO | 2010031852 | 3/2010 |

OTHER PUBLICATIONS

Cecil Textbook of Medicine, 20th edition (1996), vol. 2, pp. 2050-2057.*
Cecil Textbook of Medicine, 20th edition (1996), vol. 2, pp. 1992-1996.*
FDA mulls drug to slow late-stage Alzheimer's [online], [retrieved on Sep. 23, 2003]. Retrieved from the Internet, URL; http:||www.cnn.com|2003|HEALTH|conditions|09|24|alzheimers.drug.ap|indexhtml>.*
Vippagunta, et al. Advanced Drug Delivery Reviews 48 (2001) 3-26.*
Strohmeier et al., Arch. Pharm. (Weinheim) 318, 1985, 421-431.

* cited by examiner

*Primary Examiner* — Shawquia Young
(74) *Attorney, Agent, or Firm* — Cantor Colburn LLP

(57) ABSTRACT

The invention provides a compound of formula(I) or a pharmaceutically acceptable ester, amide, solvate or salt thereof, including a salt of such an ester or amide, and a solvate of such an ester, amide or salt. The invention also provides the use of such compounds in the treatment or prophylaxis of a condition associated with a disease or disorder associated with estrogen receptor activity. Formula(I) wherein $R^1$, $R^2$, $R^3$, $R^4$, $R^5$, $R^6$, $R^7$, $R^8$, $R^9$ and $R^{10}$ are as defined in the specification.

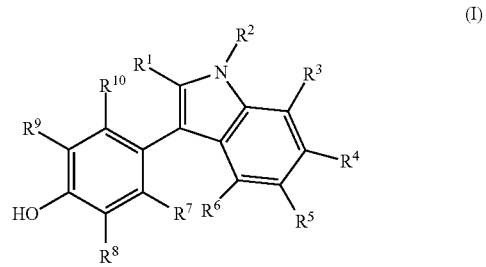

11 Claims, No Drawings

ESTROGEN RECEPTOR LIGANDS

CROSS-REFERENCE TO RELATED APPLICATIONS

This application is a U.S. National Stage application of International Application PCT/EP2010/064939 filed 6 Oct. 2010, which claims benefits of GB 0917575.3 filed 7 Oct. 2009 and GB1004377.6 filed 16 Mar. 2010.

FIELD OF INVENTION

This invention relates to compounds which are estrogen receptor ligands and are preferably selective for the estrogen receptor β isoform, to methods of preparing such compounds and to methods for using such compounds in treatment of diseases related to the estrogen receptor such as depressive disorders, anxiety disorders, Alzheimer's disease, cognitive disorders, osteoporosis, elevated blood triglyceride levels, atherosclerosis, endometriosis, urinary incontinence, autoimmune disease, and cancer of the lung, colon, breast, uterus and prostate.

BACKGROUND OF INVENTION

The estrogen receptor (ER) is a ligand activated mammalian transcription factor involved in the up and down regulation of gene expression. The natural hormone for the estrogen receptor is β-17-estradiol (E2) and closely related metabolites. Binding of estradiol to the estrogen receptor causes a dimerization of the receptor and the dimer in turn binds to estrogen response elements (ERE's) on DNA. The ER/DNA complex recruits other transcription factors responsible for the transcription of DNA downstream from the ERE into mRNA which is eventually translated into protein. Alternatively the interaction of ER with DNA may be indirect through the intermediacy of other transcription factors, most notably fos and jun. Since the expression of a large number of genes is regulated by the estrogen receptor and since the estrogen receptor is expressed in many cell types, modulation of the estrogen receptor through binding of either natural hormones or synthetic ER ligands can have profound effects on the physiology and pathophysiology of the organism.

Historically it has been believed there was only one estrogen receptor. However a second subtype (ER-β) has been discovered. While both the "classical" ER-α and the more recently discovered ER-β are widely distributed in different tissues, they nevertheless display markedly different cell type and tissue distributions. Therefore synthetic ligands which are either ER-α or ER-β selective may preserve the beneficial effects of estrogen while reducing the risk of undesirable side effects.

Estrogens are critical for sexual development in females. In addition, estrogens play an important role in maintaining bone density, regulation of blood lipid levels, and appear to have neuroprotective effects. Consequently decreased estrogen production in post-menopausal women is associated with a number of diseases such as osteoporosis, atherosclerosis, depression and cognitive disorders. Conversely certain types of proliferative diseases such as breast and uterine cancer and endometriosis are stimulated by estrogens and therefore anti-estrogens (i.e., estrogen antagonists) have utility in the prevention and treatment of these types of disorders.

The efficacy of the natural estrogen, 17β-estradiol, for the treatment of various forms of depressive illness has also been demonstrated and it has been suggested that the anti-depressant activity of estrogen may be mediated via regulation of tryptophan hydroxylase activity and subsequent serotonin synthesis (See, e.g., Lu N Z, Shlaes T A, Cundlah C, Dziennis S E, Lyle R E, Bethea C L, "Ovarian steroid action on tryptophan hydroxylase protein and serotonin compared to localization of ovarian steroid receptors in midbrain of guinea pigs." Endocrine 11:257-267, 1999). The pleiotropic nature of natural estrogen precludes its widespread, more chronic use due to the increased risk of proliferative effects on breast, uterine and ovarian tissues. The identification of the estrogen receptor, ERβ, has provided a means by which to identify more selective estrogen agents which have the desired anti-depressant activity in the absence of the proliferative effects which are mediated by ERα. Thus, it has been shown that therapeutic agents having ERβ-selectivity are potentially effective in the treatment of depression.

What is needed in the art are compounds that can produce the same positive responses as estrogen replacement therapy without the negative side effects. Also needed are estrogen-like compounds that exert selective effects on different tissues of the body.

US 2003/0220377 discloses certain indole compounds that are useful as estrogen agonists and antagonists and their potential use in the treatment of estrogen mediated disorders. JP 2001-122855 discloses certain indole compounds selectively acting on the estrogen receptor beta that may be useful in the treatment of osteoporosis.

The compounds of the present invention are ligands for estrogen receptors and as such may be useful for treatment or prevention of a variety of conditions related to estrogen functioning.

SUMMARY OF THE INVENTION

This invention provides a compound of formula (I) or a pharmaceutically acceptable ester, amide, solvate or salt thereof, including a salt of such an ester or amide, and a solvate of such an ester, amide or salt,

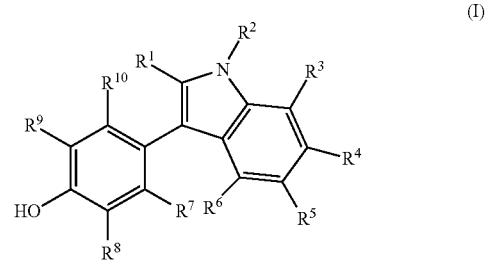

wherein $R^1$ is selected from the group consisting of halogen, cyano, nitro, $OR^A$, $N(R^B)_2$, —C(O)$C_{1-4}$alkyl, —SO$_2C_{1-4}$alkyl, $C_{1-6}$alkyl, $C_{2-6}$alkenyl, $C_{2-6}$alkynyl, halo$C_{1-6}$alkyl, dihalo$C_{1-6}$alkyl, trihalo$C_{1-6}$alkyl, halo$C_{2-6}$alkenyl, dihalo$C_{2-6}$alkenyl, trihalo$C_{2-6}$alkenyl, cyano$C_{1-6}$alkyl, $C_{1-4}$alkoxy$C_{1-6}$ alkyl, $C_{3-8}$cycloalkyl, $C_{3-8}$cycloalkyl$C_{1-6}$alkyl, phenyl, benzyl, and 5-10 membered heterocyclyl, wherein said phenyl, benzyl or heterocyclyl group can be either unsubstituted or substituted with from 1 to 3 substituents, each substituent being independently selected from the group consisting of $OR^A$, halogen, cyano, nitro, —C(O)$C_{1-4}$alkyl, $C_{1-6}$alkyl, $C_{2-6}$alkenyl, $C_{2-6}$alkynyl, halo$C_{1-6}$ alkyl, dihalo$C_{1-6}$alkyl and trihalo$C_{1-6}$alkyl;

$R^2$ is selected from the group consisting of cyano, nitro, N(OH)$_2$, —CHO, —CH=N—OH, —C(O)$C_{1-4}$alkyl optionally substituted with from 1 to 3 halogens, —SO$_2C_{1-4}$alkyl, —C(O)NH—OH, —C(NH$_2$)=N—OH, —C(CO$_2$H)=N—OH, —C(NH$_2$)=NH, —C(NH$_2$)=N—NH$_2$, —NH—C(NH$_2$)=NH, —NH—C(O)NH$_2$, —N=C(—NH—CH$_2$CH$_2$—NH—), —S—CN, —S—C(NH$_2$)=NH, —S—C(NH$_2$)=N—OH, —CO$_2$H, —CH(OH)CO$_2$H, —C(O)N(R$^C$)$_2$, —SO$_2$C$_{1-6}$alkyl, SO$_2$N(R$^C$)$_2$, —C(O)—C(O)—NH$_2$, —CH$_2$NH—CONH$_2$, —SO$_2$OR$^C$, —C(O)CO$_2$H, —CH$_2$SO$_3$H and 5-10 membered heterocyclyl wherein said heterocyclyl group can be either unsubstituted or substituted with from 1 to 3 substituents each substituent being independently selected from the group consisting of OR$^A$, halogen, cyano, nitro, C$_{1-6}$alkyl, C$_{2-6}$alkenyl, C$_{2-6}$alkynyl, haloC$_{1-6}$alkyl, dihaloC$_{1-6}$alkyl and trihaloC$_{1-6}$alkyl;

each of R$^3$, R$^4$, R$^5$, R$^6$, R$^7$, R$^8$, R$^9$ and R$^{10}$ is independently selected from the group consisting of hydrogen, OR$^A$, halogen, cyano, nitro, C$_{1-6}$alkyl, C$_{2-6}$alkenyl, C$_{2-6}$alkynyl, haloC$_{1-6}$alkyl, dihaloC$_{1-6}$alkyl and trihaloC$_{1-6}$alkyl;

each R$^A$ is independently selected from the group consisting of hydrogen, C$_{1-6}$alkyl, C$_{2-6}$alkenyl, C$_{2-6}$alkynyl, C$_{3-8}$cycloalkyl, C$_{3-8}$cycloalkylC$_{1-6}$alkyl, phenyl, benzyl and 5-10 membered heterocyclyl, each optionally substituted by from 1 to 3 halogen atoms; and each R$^B$ is independently selected from the group consisting of hydrogen, C$_{1-6}$alkyl, C$_{2-6}$alkenyl, C$_{2-6}$alkynyl, C$_{3-8}$cycloalkyl, C$_{3-8}$cycloalkylC$_{1-6}$alkyl, phenyl, benzyl and 5-10 membered heterocyclyl, each optionally substituted by from 1 to 3 halogen atoms; and each R$^C$ is independently selected from the group consisting of hydrogen and C$_{1-6}$alkyl.

Compounds of the invention have surprisingly been found to be ligands of the estrogen receptor. The compounds accordingly have use in the treatment or prophylaxis of conditions associated with estrogen receptor activity.

DETAILED DESCRIPTION OF INVENTION

The compounds of the invention may contain chiral (asymmetric) centers or the molecule as a whole may be chiral. The individual stereoisomers (enantiomers and diastereoisomers) and mixtures of these are within the scope of the present invention.

Certain compounds of the invention contain an oxime group which may be present as the (E) or (Z) oxime isomer. The individual (E) and (Z) oxime isomers and mixtures of these are within the scope of the present invention. Throughout the specification, where the oxime structure is shown with a wavy line bond, this indicates either that a single isomer is present but the stereochemistry is unknown, or that a mixture of both isomers is present.

The present invention provides compounds that are estrogen receptor ligands. The term "estrogen receptor ligand" as used herein is intended to cover any moiety which binds to an estrogen receptor. The ligand may act as an agonist, a partial agonist, an antagonist or a partial antagonist. The ligand may be ERβ selective or display mixed ERα and ERβ activity. For example, the ligand may act both as an agonist or a partial agonist of ERβ and as an antagonist or a partial antagonist of ERα. Compounds of the present invention are preferably estrogen receptor ligands that display ERβ selective agonism.

When R$^1$ represents a heterocyclyl group, this group may be saturated or unsaturated, and may contain one or more O, N and/or S atoms. It is preferably 5- or 6-membered. In one preferred embodiment, it is 6-membered or, especially, 5-membered, and is preferably unsaturated, especially aromatic. Suitable heterocyclyl groups include furyl, thienyl, pyrrolyl, pyrrolinyl, pyrrolidinyl, oxazolyl, isoxazolyl, thiazolyl, isothiazolyl, imidazolyl, imidazolinyl, imidazolidinyl, pyrazolyl, pyrazolinyl, pyrazolidinyl, pyridyl, morpholinyl, and piperidyl, with thienyl, isothiazole and, especially, isoxazolyl, being particularly preferred. Preferred substituents for a heterocyclyl group include 1 to 3, for example 1 or 2, substituents, each substituent being selected from the group consisting of OR$^A$, halogen, cyano, —C(O)C$_{1-4}$alkyl, C$_{1-4}$alkyl, C$_{2-4}$alkenyl, C$_{2-4}$alkynyl, haloC$_{1-4}$alkyl, dihaloC$_{1-4}$alkyl and trihaloC$_{1-4}$alkyl. Especially preferred substituents are selected from halogen, cyano, C$_{1-4}$alkyl (especially methyl), —C(O)C$_{1-4}$alkyl, and OR$^A$ in which R$^A$ preferably represents a hydrogen atom or a C$_{1-4}$alkyl group. More especially preferred substituents are selected from halogen, cyano and C$_{1-4}$alkyl (especially methyl or ethyl). Thus, in one preferred embodiment, R$^1$ is one of the above mentioned groups substituted by two methyl groups, for example 3,5-dimethylisoxazol-4-yl, 2,4-dimethyl-thien-3-yl, or 3,5-dimethylisothiazol-4-yl.

Preferred substituents for a phenyl group R$^1$ include those mentioned above for a heterocyclyl group R$^1$.

When R$^2$ represents a heterocyclyl group, this group may for example be one of the preferred groups mentioned above for R$^1$.

Unless otherwise stated, each R$^A$ is preferably independently selected from the group consisting of hydrogen, C$_{1-4}$alkyl, C$_{2-4}$alkenyl, C$_{2-4}$alkynyl, C$_{3-6}$cycloalkyl, phenyl and benzyl. Preferably each R$^A$ independently represents hydrogen or C$_{1-4}$alkyl, especially methyl.

Unless otherwise stated, each R$^B$ is preferably independently selected from the group consisting of hydrogen and C$_{1-4}$alkyl, especially methyl.

Unless otherwise stated, each R$^C$ is preferably independently selected from the group consisting of hydrogen and C$_{1-4}$alkyl, especially methyl. In one embodiment, each R$^C$ represents hydrogen.

Preferably R$^1$ is selected from the group consisting of C$_{1-6}$alkyl, C$_{2-6}$alkenyl, C$_{2-6}$alkynyl, phenyl, or a 5-10 membered heterocyclyl, wherein said phenyl or heterocyclyl group can be either unsubstituted or substituted as above. More preferably, R$^1$ is selected from the group consisting of C$_{1-6}$alkyl, C$_{2-6}$alkenyl, C$_{2-6}$alkynyl, phenyl, or a 5-10 membered heterocyclyl, wherein said phenyl or heterocyclyl group can either be unsubstituted or substituted with from 1 to 2 substituents, each substituent being independently selected from cyano or C$_{1-6}$alkyl. Most preferably, R$^1$ represents a phenyl or 5-6 membered heterocyclyl group, wherein said phenyl or heterocyclyl group is substituted with from 1 to 2 substituents, said substituent or substitutents being C$_{1-6}$alkyl. In a further preferred embodiment, R$^1$ represents a phenyl or 5-membered heterocyclyl group, wherein said phenyl or heterocyclyl group is substituted with 2 substituents, said substituents being methyl. For example, R$^1$ may be 2,5-dimethylphenyl, 3,5-dimethylisoxazol-4-yl, 2,4-dimethyl-thien-3-yl, or 3,5-dimethylisothiazol-4-yl.

In one embodiment of the invention, R$^2$ is selected from the group consisting of cyano, —CHO, —CH=N—OH, —C(O)NH—OH, —C(NH$_2$)=N—OH, —C(CO$_2$H)=N—OH, —C(NH$_2$)=NH, —C(NH$_2$)=N—NH$_2$, —NH—C(NH$_2$)=NH, —NH—C(O)NH$_2$, —S—CN, —S—C(NH$_2$)=NH, —S—C(NH$_2$)=N—OH, —CO$_2$H, —CH(OH)CO$_2$H, —C(O)N(R$^C$)$_2$, SO$_2$N(R$^C$)$_2$, —C(O)—C(O)—NH$_2$, —CH$_2$NH—CONH$_2$, —SO$_2$C$_{1-6}$alkyl, —SO$_2$OR$^C$, —C(O)CO$_2$H, —CH$_2$SO$_3$H and 5-6 membered heterocyclyl wherein said heterocyclyl group can be either unsubstituted or substituted with from 1 to 3 substituents each substituent being independently selected from the group consisting of OR$^A$, halogen, cyano, nitro, C$_{1-6}$alkyl, C$_{2-6}$alkenyl, C$_{2-6}$alkynyl, haloC$_{1-6}$alkyl, dihaloC$_{1-6}$alkyl and trihaloC$_{1-6}$alkyl. In a preferred embodiment of the invention, $R^2$ represents cyano, —CH═N—OH, —C(O)N($R^C$)$_2$, —C(NH$_2$)═N—OH, SO$_2$N($R^C$)$_2$, —SO$_2$C$_{1-6}$alkyl, —SO$_2$O$R^C$ or a 5-6 membered heterocyclyl group being either unsubstituted or substituted with from 1 to 3 substituents each substituent being independently selected from the group consisting of O$R^4$, halogen, cyano, nitro, C$_{1-6}$alkyl, C$_{2-6}$alkenyl, C$_{2-6}$alkynyl, haloC$_{1-6}$alkyl, dihaloC$_{1-6}$alkyl and trihaloC$_{1-6}$alkyl. More preferably, $R^2$ is selected from the group consisting of cyano, —CH═N—OH, —C(O)N($R^C$)$_2$, —C(NH$_2$)═N—OH, SO$_2$N($R^C$)$_2$, —SO$_2$C$_{1-4}$alkyl and —SO$_2$O$R^C$.

In an alternative embodiment of the invention, $R^2$ is selected from the group consisting of cyano, nitro, N(OH)$_2$, —CHO, —C(O)C$_{1-4}$alkyl optionally substituted with from 1 to 3 halogens, —SO$_2$C$_{1-4}$alkyl, —C(O)NH—OH, —C(NH$_2$)═N—OH, —C(CO$_2$H)═N—OH, —C(NH$_2$)═NH, —C(NH$_2$)═N—NH$_2$, —NH—C(NH$_2$)═NH, —NH—C(O)NH$_2$, —N═C(—NH—CH$_2$CH$_2$—NH—), —S—CN, —S—C(NH$_2$)═NH, —S—C(NH$_2$)═N—OH, —CO$_2$H, —CH(OH)CO$_2$H, —C(O)N($R^C$)$_2$, —SO$_2$C$_{1-6}$alkyl, —C(O)—C(O)—NH$_2$, —CH$_2$NH—CONH$_2$, —SO$_2$O$R^C$, —C(O)CO$_2$H, —CH$_2$SO$_3$H and 5-10 membered heterocyclyl wherein said heterocyclyl group can be either unsubstituted or substituted with from 1 to 3 substituents each substituent being independently selected from the group consisting of O$R^4$, halogen, cyano, nitro, C$_{1-6}$alkyl, C$_{2-6}$alkenyl, C$_{2-6}$alkynyl, haloC$_{1-6}$alkyl, dihaloC$_{1-6}$alkyl and trihaloC$_{1-6}$alkyl. In this embodiment, $R^2$ preferably represents cyano, —C(O)N($R^C$)$_2$, —C(NH$_2$)═N—OH, —SO$_2$C$_{1-6}$alkyl, —SO$_2$O$R^C$ or a 5-6 membered heterocyclyl group being either unsubstituted or substituted with from 1 to 3 substituents each substituent being independently selected from the group consisting of O$R^4$, halogen, cyano, nitro, C$_{1-6}$alkyl, C$_{2-6}$alkenyl, C$_{2-6}$alkynyl, haloC$_{1-6}$alkyl, dihaloC$_{1-6}$alkyl and trihaloC$_{1-6}$alkyl. More preferably, in this embodiment, $R^2$ is selected from the group consisting of cyano, —C(O)N($R^C$)$_2$, —C(NH$_2$)═N—OH, —SO$_2$C$_{1-4}$alkyl and —SO$_2$O$R^C$.

Preferably $R^2$ is selected from —C(NH$_2$)═N—OH or —C(O)N($R^C$)$_2$, especially —C(NH$_2$)═N—OH or C(O)NH$_2$, especially —C(NH$_2$)═N—OH.

Preferably each of $R^3$, $R^4$, $R^5$, $R^6$, $R^7$, $R^8$, $R^9$ and $R^{10}$ is selected from the group consisting of hydrogen, O$R^4$, halogen, cyano, C$_{1-4}$alkyl, for example methyl, haloC$_{1-4}$alkyl, for example chloro- or fluoro-methyl, dihaloC$_{1-4}$alkyl, for example dichloro- or difluoromethyl, and trihaloC$_{1-4}$alkyl, for example trichloro- or trifluoromethyl. Preferably each of $R^3$, $R^4$, $R^5$, $R^6$, $R^7$, $R^8$, $R^9$ and $R^{10}$ is selected from the group consisting of hydrogen, OH, halogen, cyano, methyl, or trifluoromethyl. Most preferably each of $R^3$, $R^4$, $R^5$, $R^6$, $R^7$, $R^8$, $R^9$ and $R^{10}$ independently represents hydrogen and/or halogen, especially chlorine or, particularly, fluorine. In a particularly preferred embodiment, each of $R^3$, $R^4$, $R^5$ and $R^6$ represents hydrogen. In a further preferred embodiment, each of $R^7$, $R^8$, $R^9$ and $R^{10}$ represents hydrogen, and one or two of $R^7$, $R^8$, $R^9$ and $R^{10}$ represents halogen, especially fluorine, and the remainder of $R^7$, $R^8$, $R^9$ and $R^{10}$ represent hydrogen.

Compounds of the formula (I) include, but are not limited to, the compounds specifically named in the Examples herein.

Further compounds of the formula (I) include, but are not limited to, the following compounds:

2-(2,5-dimethyl-1H-pyrrol-1-yl)-N'-hydroxy-3-(4-hydroxyphenyl)-1H-indole-1-carboximidamide;
2-(1,4-dimethyl-1H-pyrazol-5-yl)-N'-hydroxy-3-(4-hydroxyphenyl)-1H-indole-1-carboximidamide;
2-(2,5-dimethylpyrrolidin-1-yl)-N'-hydroxy-3-(4-hydroxyphenyl)-1H-indole-1-carboximidamide;
N'-hydroxy-3-(4-hydroxyphenyl)-2-(pyrrolidin-1-yl)-1H-indole-1-carboximidamide;
5-chloro-2-(3,5-dimethylisoxazol-4-yl)-N'-hydroxy-3-(4-hydroxyphenyl)-1H-indole-1-carboximidamide;
2-(5-fluoro-2,4-dimethylfuran-3-yl)-N'-hydroxy-3-(4-hydroxyphenyl)-1H-indole-1-carboximidamide;
2-(5-chloro-2,4-dimethylfuran-3-yl)-N'-hydroxy-3-(4-hydroxyphenyl)-1H-indole-1-carboximidamide;
2-(1,3-dimethyl-1H-pyrrol-2-yl)-N'-hydroxy-3-(4-hydroxyphenyl)-1H-indole-1-carboximidamide;
2-(1,4-dimethyl-1H-imidazol-5-yl)-N'-hydroxy-3-(4-hydroxyphenyl)-1H-indole-1-carboximidamide;
2-(2,5-dimethyl-1H-imidazol-1-yl)-N'-hydroxy-3-(4-hydroxyphenyl)-1H-indole-1-carboximidamide;
2-(5-fluoro-2,4-dimethylfuran-3-yl)-3-(4-hydroxyphenyl)-1H-indole-1-carboxamide;
2-(5-chloro-2,4-dimethylfuran-3-yl)-3-(4-hydroxyphenyl)-1H-indole-1-carboxamide;
2-(1,3-dimethyl-1H-pyrrol-2-yl)-3-(4-hydroxyphenyl)-1H-indole-1-carboxamide;
2-(1,4-dimethyl-1H-imidazol-5-yl)-3-(4-hydroxyphenyl)-1H-indole-1-carboxamide;
2-(2,5-dimethyl-1H-imidazol-1-yl)-3-(4-hydroxyphenyl)-1H-indole-1-carboxamide;

or a pharmaceutically acceptable ester, amide, solvate or salt thereof, including a salt of such an ester or amide, and a solvate of such an ester, amide or salt thereof.

In the compounds listed above and in the Examples, the compound names were generated in accordance with IUPAC by the ACD Labs 8.0/name program, version 8.05 and/or with ISIS DRAW Autonom 2000 and/or ChemBioDraw Ultra version 11.0.

Depending upon the substituents present in compounds of the formula I, the compounds may form esters, amides, carbamates and/or salts. Salts and solvates of compounds of formula (I) which are suitable for use in medicine are those wherein a counterion or associated solvent is pharmaceutically acceptable. However, salts and solvates having non-pharmaceutically acceptable counterions or associated solvents are within the scope of the present invention, for example, for use as intermediates in the preparation of the compounds of formula (I) and their pharmaceutically acceptable salts, solvates and physiologically functional derivatives. By the term "physiologically functional derivative" is meant a chemical derivative of a compound of formula (I) having the same physiological function as the free compound of formula (I), for example, by being convertible in the body thereto. Esters, amides and carbamates are examples of physiologically functional derivatives.

Suitable salts according to the invention include those formed with organic or inorganic acids or bases. In particular, suitable salts formed with acids according to the invention include those formed with mineral acids, strong organic carboxylic acids, such as alkanecarboxylic acids of 1 to 4 carbon atoms which are unsubstituted or substituted, for example, by halogen, such as saturated or unsaturated dicarboxylic acids, such as hydroxycarboxylic acids, such as amino acids, or with organic sulfonic acids, such as (C$_1$-C$_4$)-alkyl- or aryl-sulfonic acids which are unsubstituted or substituted, for example by halogen. Pharmaceutically acceptable acid addition salts include those formed from hydrochloric, hydrobromic, sulphuric, nitric, citric, tartaric, acetic, phosphoric, lactic, pyruvic, acetic, trifluoroacetic, succinic, perchloric, fumaric, maleic, glycolic, lactic, salicylic, oxaloacetic, methanesulfonic, ethanesulfonic, p-toluenesulfonic, formic, benzoic, malonic, naphthalene-2-sulfonic, benzenesulfonic, isethionic, ascorbic, malic, phthalic, aspartic, and glutamic acids, lysine and arginine. Other acids such as oxalic, while not in themselves pharmaceutically acceptable, may be useful as intermediates in obtaining the compounds of the invention and their pharmaceutical acceptable acid addition salts.

Pharmaceutically acceptable base salts include ammonium salts, alkali metal salts, for example those of potassium and sodium, alkaline earth metal salts, for example those of calcium and magnesium, and salts with organic bases, for example dicyclohexylamine, N-methyl-D-glucomine, morpholine, thiomorpholine, piperidine, pyrrolidine, a mono-, di- or tri-lower alkylamine, for example ethyl-, tert-butyl-, diethyl-, diisopropyl-, triethyl-, tributyl- or dimethyl-propylamine, or a mono-, di- or trihydroxy lower alkylamine, for example mono-, di- or triethanolamine. Corresponding internal salts may furthermore be formed.

Compounds of formula (I) may have an appropriate group converted to an ester, an amide or a carbamate. Thus typical ester and amide groups formed from an acid group in the compound of the formula I include —$COOR^B$, —$CONR^B_2$, —$SO_2OR^B$, or —$SO_2N(R^B)_2$, while typical ester and amide and carbamate groups formed from an —OH or —$NHR^B$ group in the compound of the formula I include —$OC(O)R^B$, —$NR^BC(O)R^B$, —$NR^BCO_2R^B$—$OSO_2R^B$, and —$NR^BSO_2R^B$, where $R^B$ has one of the meanings given above.

Those skilled in the art of organic chemistry will appreciate that many organic compounds can form complexes with solvents in which they are reacted or from which they are precipitated or crystallized. These complexes are known as "solvates". For example, a complex with water is known as a "hydrate".

A compound which, upon administration to the recipient, is capable of being converted into a compound of formula (I) as described above, or an active metabolite or residue thereof, is known as a "prodrug". A prodrug may, for example, be converted within the body, e.g. by hydrolysis in the blood, into its active form that has medical effects. Pharmaceutical acceptable prodrugs are described in T. Higuchi and V. Stella, Prodrugs as Novel Delivery Systems, Vol. 14 of the A.C.S. Symposium Series (1976); "Design of Prodrugs" ed. H. Bundgaard, Elsevier, 1985; and in Edward B. Roche, ed., Bioreversible Carriers in Drug Design, American Pharmaceutical Association and Pergamon Press, 1987, which are incorporated herein by reference.

The following definitions apply to the terms as used throughout this specification, unless otherwise limited in specific instances.

As used herein, the term "alkyl" means both straight and branched chain saturated hydrocarbon groups. Examples of alkyl groups include methyl, ethyl, n-propyl, iso-propyl, n-butyl, t-butyl, i-butyl, sec-butyl, pentyl and hexyl groups. Among unbranched alkyl groups, there are preferred methyl, ethyl, n-propyl, iso-propyl, n-butyl, and n-pentyl groups. Among branched alkyl groups, there may be mentioned iso-propyl, t-butyl, i-butyl, 1-ethylpropyl and 1-ethylbutyl groups.

As used herein, the term "alkoxy" means the group O-alkyl, where "alkyl" is used as described above. Examples of alkoxy groups include methoxy and ethoxy groups. Other examples include propoxy and butoxy.

As used herein, the term "alkenyl" means both straight and branched chain unsaturated hydrocarbon groups with at least one carbon carbon double bond. Examples of alkenyl groups include ethenyl, propenyl, butenyl, pentenyl and hexenyl. Preferred alkenyl groups include ethenyl, 1-propenyl, 2-propenyl and but-2-enyl.

As used herein, the term "alkynyl" means both straight and branched chain unsaturated hydrocarbon groups with at least one carbon carbon triple bond. Examples of alkynyl groups include ethynyl, propynyl, butynyl, pentynyl and hexynyl. Preferred alkynyl groups include ethynyl, 1-propynyl and 2-propynyl.

As used herein, the term "cycloalkyl" means a saturated group in a ring system. A cycloalkyl group can be monocyclic or bicyclic. A bicyclic group may, for example, be fused or bridged. Examples of monocyclic cycloalkyl groups include cyclopropyl, cyclobutyl and cyclopentyl. Other examples of monocyclic cycloalkyl groups are cyclohexyl, cycloheptyl and cyclooctyl. Examples of bicyclic cycloalkyl groups include bicyclo [2.2.1]hept-2-yl. Preferably, the cycloalkyl group is monocyclic.

As used herein, the term "aryl" means a monocyclic or bicyclic aromatic carbocyclic group. Examples of aryl groups include phenyl and naphthyl. A naphthyl group may be attached through the 1 or the 2 position. In a bicyclic aromatic group, one of the rings may, for example, be partially saturated. Examples of such groups include indanyl and tetrahydronaphthyl. Specifically, the term $C_{5-10}$ aryl is used herein to mean a group comprising from 5 to 10 carbon atoms in a monocyclic or bicyclic aromatic group. A particularly preferred $C_{5-10}$ aryl group is phenyl.

As used herein, the term "halogen" means fluorine, chlorine, bromine or iodine. Fluorine, chlorine and bromine are particularly preferred.

As used herein, the term "haloalkyl" means an alkyl group having a halogen substituent, the terms "alkyl" and "halogen" being understood to have the meanings outlined above. Similarly, the term "dihaloalkyl" means an alkyl group having two halogen substituents and the term "trihaloalkyl" means an alkyl group having three halogen substituents. Examples of haloalkyl groups include fluoromethyl, chloromethyl, bromomethyl, fluoromethyl, fluoropropyl and fluorobutyl groups; examples of dihaloalkyl groups include difluoromethyl and difluoroethyl groups; examples of triihaloalkyl groups include trifluoromethyl and trifluoroethyl groups.

As used herein, the term "heterocyclyl" means an aromatic or a non-aromatic cyclic group of carbon atoms wherein from one to three of the carbon atoms is/are replaced by one or more heteroatoms independently selected from nitrogen, oxygen or sulfur. A heterocyclyl group may, for example, be monocyclic or bicyclic. In a bicyclic heterocyclyl group there may be one or more heteroatoms in each ring, or only in one of the rings. A heteroatom may for example be O or N. Heterocyclyl groups containing a suitable nitrogen atom include the corresponding N-oxides.

Examples of monocyclic non-aromatic heterocyclyl groups (also referred to as monocyclic heterocycloalkyl rings) include aziridinyl, azetidinyl, pyrrolidinyl, imidazolidinyl, pyrazolidinyl, piperidinyl, piperazinyl, tetrahydrofuranyl, tetrahydropyranyl, morpholinyl, thiomorpholinyl and azepanyl.

Examples of bicyclic heterocyclyl groups in which one of the rings is non-aromatic include dihydrobenzofuranyl, indanyl, indolinyl, isoindolinyl, tetrahydroisoquinolinyl, tetrahydroquinolyl and benzoazepanyl.

Examples of monocyclic aromatic heterocyclyl groups (also referred to as monocyclic heteroaryl groups) include furanyl, thienyl, pyrrolyl, oxazolyl, thiazolyl, imidazolyl, oxadiazolyl, thiadiazolyl, pyridyl, triazolyl, triazinyl, pyridazyl, isothiazolyl, isoxazolyl, pyrazinyl, pyrazolyl and pyrimidinyl.

Examples of bicyclic aromatic heterocyclyl groups (also referred to as bicyclic heteroaryl groups) include quinoxalinyl, quinazolinyl, pyridopyrazinyl, benzoxazolyl, benzothiophenyl, benzimidazolyl, naphthyridinyl, quinolinyl, benzofuranyl, indolyl, benzothiazolyl, oxazolyl[4,5-b]pyridiyl, pyridopyrimidinyl, isoquinolinyl and benzodroxazole.

Examples of preferred heterocyclyl groups include piperidinyl, tetrahydrofuranyl, tetrahydropyranyl, pyridyl, pyrimidinyl and indolyl. Preferred heterocyclyl groups also include thienyl, thiazolyl, furanyl, pyrazolyl, pyrrolyl, isoxazolyl and imidazolyl.

As used herein the term "cycloalkylalkyl" means a group cycloalkyl-alkyl-attached through the alkyl group, "cycloalkyl" and "alkyl" being understood to have the meanings outlined above.

As mentioned above, the compounds of the invention have activity as estrogen receptor ligands. The compounds of the invention have activity as estrogen receptor modulators, and may be agonists, partial agonists, antagonists, or partial antagonists of the estrogen receptor. Particularly preferred compounds of the invention have activity as an agonist or a partial agonist of ERβ. Preferred compounds of this type are selective agonists of the estrogen receptor-beta (ERβ).

The compounds of the invention may thus be used in the treatment of diseases or disorders associated with estrogen receptor activity. In particular, the compounds of the invention that are agonists or partial agonists of the estrogen receptor may be used in the treatment of diseases or disorders for which selective agonists or partial agonists of the estrogen receptor are indicated. The compounds of the invention that are antagonists or partial antagonists of the estrogen receptor may be used in the treatment of diseases or disorders for which selective antagonists or partial antagonists of the estrogen receptor are indicated.

Clinical conditions for which an agonist or partial agonist is indicated include, but are not limited to, bone loss, bone fractures, osteoporosis, cartilage degeneration, endometriosis, uterine fibroid disease, hot flashes, increased levels of LDL cholesterol, cardiovascular disease, impairment of cognitive functioning, cerebral degenerative disorders, restenosis, gynecomastia, vascular smooth muscle cell proliferation, obesity, incontinence, anxiety, depression, autoimmune disease, inflammation, IBD, IBS, sexual dysfunction, hypertension, retinal degeneration, and lung, colon, breast, uterus, and prostate cancer, and/or disorders related to estrogen functioning.

The compounds of the invention find particular application in the treatment or prophylaxis of the following: bone loss, bone fractures, osteoporosis, cartilage degeneration, endometriosis, uterine fibroid disease, hot flashes, increased levels of LDL cholesterol, cardiovascular disease, impairment of cognitive functioning, age-related mild cognitive impairment, cerebral degenerative disorders, restenosis, gynecomastia, vascular smooth muscle cell proliferation, obesity, incontinence, anxiety, depression, perimenopausal depression, post-partum depression, premenstrual syndrome, manic depression, dementia, obsessive compulsive behavior, attention deficit disorder, attention deficit hyperactivity disorder, sleep disorders, irritability, impulsivity, anger management, hearing disorders, multiple sclerosis, Parkinson's disease, Alzheimer's disease, Huntington's disease, amyotrophic lateral sclerosis, spinal cord injury, stroke, autoimmune disease, inflammation, IBD, IBS, sexual dysfunction, hypertension, retinal degeneration, lung cancer, colon cancer, breast cancer, uterus cancer, prostate cancer, and the bile duct cancer form named cholangiocarcinoma. The compounds of the invention also find particular application in the treatment or prophylaxis of the following: benign prostatic hyperplasia, lower urinary tract symptoms, overactive bladder, interstitial cystitis, painful bladder symptoms, vaginal atrophy, wound healing, chronic pain, sepsis, inflammatory and neuropathic pain, ovarian cancer, melanoma, and lymphoma (B-cell lymphoma, T-cell lymphoma).

In combination with drugs that are known to induce vasomotor symptoms, the compounds of the invention find utility as follows: in combination with SERMs such as tamoxifen, in its use for the treatment of breast cancer, and raloxifene, used for the treatment and/or prevention of osteoporosis, to alleviate SERM-induced vasomotor symptoms; in combination with an aromatase inhibitor, used for the treatment of breast cancer or endometriosis, to alleviate aromatase inhibitor-induced vasomotor symptoms; and in male prostate cancer patients that have undergone androgen deprivation therapy.

In one embodiment of the invention, the present compounds finds particular application in the treatment or prophylaxis of depression, perimenopausal depression, post-partum depression, premenstrual syndrome and manic depression.

The treatment or prophylaxis of hot flashes (or hot flushes) in males, is preferable for patients that have had an androgen ablation for treatment of prostate cancer.

The phrase "depression" includes but is not limited to, major depressive disorder, dysthymic disorder, bipolar disorder, cyclothymic disorder, mood disorder due to a general medical condition, substance-induced mood disorder, seasonal affective disorder (SAD), postpartum depression and premenstrual dysphoric disorder.

The invention also provides a method for the treatment or prophylaxis of a condition in a mammal mediated by an estrogen receptor, which comprises administering to the mammal a therapeutically effective amount of a compound according to the invention. Clinical conditions mediated by an estrogen receptor that may be treated by the method of the invention are preferably those described above.

The invention also provides the use of a compound according to the invention, for the manufacture of a medicament for the treatment or prophylaxis of a condition mediated by an estrogen receptor. Clinical conditions mediated by an estrogen receptor that may be treated by the method of the invention are preferably those described above.

The amount of active ingredient which is required to achieve a therapeutic effect will, of course, vary with the particular compound, the route of administration, the subject under treatment, including the type, species, age, weight, sex, and medical condition of the subject and the renal and hepatic function of the subject, and the particular disorder or disease being treated, as well as its severity. An ordinarily skilled physician, veterinarian or clinician can readily determine and prescribe the effective amount of the drug required to prevent, counter or arrest the progress of the condition.

Oral dosages of the present invention, when used for the indicated effects, will range between about 0.01 mg per kg of body weight per day (mg/kg/day) to about 100 mg/kg/day, preferably 0.01 mg per kg of body weight per day (mg/kg/day) to 10 mg/kg/day, and most preferably 0.1 to 5.0 mg/kg/day, for adult humans. For oral administration, the compositions are preferably provided in the form of tablets or other forms of presentation provided in discrete units containing 0.01, 0.05, 0.1, 0.5, 1.0, 2.5, 5.0, 10.0, 15.0, 25.0, 50.0, 100, and 500 milligrams of the active ingredient for the symptomatic adjustment of the dosage to the patient to be treated. A medicament typically contains from about 0.01 mg to about 500 mg of the active ingredient, preferably from about 1 mg to about 100 mg of active ingredient. Intravenously, the most preferred doses will range from about 0.1 to about 10 mg/kg/minute during a constant rate infusion. Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

While it is possible for the active ingredient to be administered alone, it is preferable for it to be present in a pharmaceutical formulation or composition. Accordingly, the invention provides a pharmaceutical formulation comprising a compound according to the invention, and a pharmaceutically acceptable diluent, excipient or carrier (collectively referred to herein as "carrier" materials). Pharmaceutical compositions of the invention may take the form of a pharmaceutical formulation as described below.

The pharmaceutical formulations according to the invention include those suitable for oral, parenteral (including subcutaneous, intradermal, intramuscular, intravenous [bolus or infusion], and intraarticular), inhalation (including fine particle dusts or mists which may be generated by means of various types of metered does pressurized aerosols), nebulizers or insufflators, rectal, intraperitoneal and topical (including dermal, buccal, sublingual, and intraocular) administration, although the most suitable route may depend upon, for example, the condition and disorder of the recipient.

The formulations may conveniently be presented in unit dosage form and may be prepared by any of the methods well known in the art of pharmacy. All methods include the step of bringing the active ingredient into association with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets, pills or tablets each containing a predetermined amount of the active ingredient; as a powder or granules; as a solution or a suspension in an aqueous liquid or a non-aqueous liquid, for example as elixirs, tinctures, suspensions or syrups; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein. The present compounds can, for example, be administered in a form suitable for immediate release or extended release. Immediate release or extended release can be achieved by the use of suitable pharmaceutical compositions comprising the present compounds, or, particularly in the case of extended release, by the use of devices such as subcutaneous implants or osmotic pumps. The present compounds can also be administered liposomally.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate, calcium sulfate, sorbitol, glucose and/or lactose and/or other excipients, binders, extenders, disintegrants, diluents and lubricants such as those known in the art. Suitable binders include starch, gelatin, natural sugars such as glucose or beta-lactose, corn sweeteners, natural and synthetic gums such as acacia, tragacanth or sodium alginate, carboxymethylcellulose, poly-ethylene glycol, waxes and the like. Disintegrators include without limitation starch, methylcellulose, agar, bentonite, xanthan gum and the like. The compounds of formula (I) can also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g. Carbopol 934). Lubricants, glidants, flavors, coloring agents and stabilizers may also be added for ease of fabrication and use. Lubricants used in these dosage forms include sodium oleate, sodium stearate, magnesium stearate, sodium benzoate, sodium acetate, sodium chloride and the like. For oral administration in liquid form, the oral drug components can be combined with any oral, non-toxic, pharmaceutically acceptable inert carrier such as ethanol, glycerol, water, and the like.

The compounds of the present invention can also be administered in the form of liposome delivery systems, such as small unilamellar vesicles, large unilamellar vesicles and multilamellar vesicles. Liposomes can be formed from a variety of phospholipids, 1,2-dipalmitoylphosphatidylcholine, phosphatidyl ethanolamine (cephaline), or phosphatidylcholine (lecithin).

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example saline or water-for-injection, immediately prior to use. Extemporaneous injection solutions and suspensions may be prepared from sterile powders, granules and tablets of the kind previously described. Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor.

Exemplary compositions for nasal, aerosol or inhalation administration include solutions in saline, which can contain, for example, benzyl alcohol or other suitable preservatives, absorption promoters to enhance bioavailability, and/or other solubilizing or dispersing agents such as those known in the art.

Formulations for rectal administration may be presented as a suppository with the usual carriers such as cocoa butter, synthetic glyceride esters or polyethylene glycol. Such carriers are typically solid at ordinary temperatures, but liquefy and/or dissolve in the rectal cavity to release the drug.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerine or sucrose and acacia. Exemplary compositions for topical administration include a topical carrier such as Plastibase (mineral oil gelled with polyethylene).

Preferred unit dosage formulations are those containing an effective dose, as hereinbefore recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavouring agents.

Whilst a compound of the invention may be used as the sole active ingredient in a medicament, it is also possible for the compound to be used in combination with one or more further active agents. Such further active agents may be further compounds according to the invention, or they may be different therapeutic agents, for example an antidepressant, an anxiolytic, an anti-psychotic, an agent useful in the prevention or treatment of osteoporosis, an agent useful in the prevention or treatment of cancer or other pharmaceutically active material. For example, the compounds of the instant invention may be effectively administered in combination with effective amounts of other agents such as an antidepressant, an anxiolytic, an anti-psychotic, an organic bisphosphonate or a cathepsin K inhibitor. In one preferred embodiment, the compounds of the invention may be effectively administered in combination with an effective amount of an antidepressant. Nonlimiting examples of antidepressants include noradrenaline reuptake inhibitors (NRI), selective serotonin reuptake inhibitors, monoamine oxidase inhibitors, tricyclic antidepressants (TCA), dopamine reuptake inhibitors (DRI), opioids, selective seretonic reuptake enhancers, tetracyclic antidepressants, reversible inhibitors of monoamine oxidase, melatonin agonists, serotonin and noradrenaline reuptake inhibitors (SNRI), corticotropin releasing factor antagonists, $\alpha$-adrenoreceptor antagonists, 5HT1$\alpha$ receptor agonists and antagonists, lithium and atypical anti-psychotics. Examples of antidepressants of the SSRI class include Fluoxetine and Sertraline; examples of antidepressants of the SNRI class Venlafaxine, Citalopram, Paroxetine, Escitalopram, Fluvoxamine; examples of antidepressants of the SNRI class include Duloxetine; examples of antidepressants of the DRI and NRI classes include Bupropion; examples of antidepressants of the TCA class include Amitriptyline and Dothiepin (Dosulepin). Examples of atypical antipsychotics include: Clozapine, Olanzapine, Risperidone, Quetiapine, Ziprasidone and Dopamine partial agonists. Nonlimiting examples of anxiolytics include benzodiazepines and non-benzodiazapines. Examples of benzodiazepines include lorazepam, alprazolam, and diazepam. Examples of non-benzodiazapines include Buspirone (Buspar®), barbiturates and meprobamate. One or more of those further anti-depressants may be used in combination.

Examples of anti-cancer agents include tamoxifene or an aromatase inhibitor, used in treatment of breast cancer.

In the event that hot flashes are induced by a particular treatment, a compound of the invention may be used in combination therapy with the agent of such treatment. Nonlimiting examples of such combination treatment therapies include: a compound of the invention in combination with tamoxifene treatment of breast cancer, a compound of the invention in combination with aromatase inhibitor treatment of breast cancer or a compound of the invention in combination with raloxifene treatment of osteoporosis.

Nonlimiting examples of above-mentioned organic bisphosphonates include adendronate, clodronate, etidronate, ibandronate, incadronate, minodronate, neridronate, risedronate, piridronate, pamidronate, tiludronate, zoledronate, pharmaceutically acceptable salts or esters thereof, and mixtures thereof. Preferred organic biphosphonates include alendronate and pharmaceutically acceptable salts and mixtures thereof. Most preferred is alendronate monosodium trihydrate.

The precise dosage of the bisphosphonate will vary with the dosing schedule, the oral potency of the particular bisphosphonate chosen, the age, size, sex and condition of the mammal or human, the nature and severity of the disorder to be treated, and other relevant medical and physical factors. Thus, a precise pharmaceutically effective amount cannot be specified in advance and can be readily determined by the caregiver or clinician. An appropriate amount can be determined by routine experimentation from animal models and human clinical studies. Generally, an appropriate amount of bisphosphonate is chosen to obtain a bone resorption inhibiting effect, i.e. a bone resorption inhibiting amount of the bisphonsphonate is administered. For humans, an effective oral dose of bisphosphonate is typically from about 1.5 to about 6000 µg/kg of body weight and preferably about 10 to about 2000 µg/kg of body weight.

For human oral compositions comprising alendronate, pharmaceutically acceptable salts thereof, or pharmaceutically acceptable derivatives thereof, a unit dosage typically comprises from about 8.75 mg to about 140 mg of the alendronate compound, on an alendronic acid active weight basis, i.e. on the basis of the corresponding acid.

The compounds of the present invention can be used in combination with other agents useful for treating estrogen-mediated conditions. The individual components of such combinations can be administered separately at different times during the course of therapy or concurrently in divided or single combination forms. The present invention is therefore to be understood as embracing all such regimes of simultaneous or alternating treatment and the term "administering" is to be interpreted accordingly. It will be understood that the scope of combinations of the compounds of this invention with other agents useful for treating estrogen-mediated conditions includes in principle any combination with any pharmaceutical composition useful for treating disorders related to estrogen functioning.

The above other therapeutic agents, when employed in combination with the compounds of the present invention, may be used, for example, in those amounts indicated in the Physicians' Desk Reference (PDR) or as otherwise determined by one of ordinary skill in the art.

Where the compounds of the invention are utilized in combination with one or more other therapeutic agent(s), either concurrently or sequentially, the following combination ratios and dosage ranges are preferred:

When combined with an antidepressant, an anxiolytic, an anti-psychotic, an organic bisphosphonate or a cathepsin K inhibitor, the compounds of formula (I) may be employed in a weight ratio to the additional agent within the range from about 10:1 to about 1:10.

The compounds of the invention as described above also find use, optionally in labelled form, as a diagnostic agent for the diagnosis of conditions associated with malfunction of the estrogen receptor. For example, such a compound may be radioactively labelled.

The compounds of the invention as described above, optionally in labelled form, also find use as a reference compound in methods of discovering other agonists, partial agonists, antagonists or partial antagonists of the estrogen receptor. Thus, the invention provides a method of discovering a ligand of the estrogen receptor which comprises use of a compound of the invention or a compound of the invention in labelled form, as a reference compound. For example, such a method may involve a competitive binding experiment in which binding of a compound of the invention to the estrogen receptor is reduced by the presence of a further compound which has estrogen receptor-binding characteristics, for example stronger estrogen receptor-binding characteristics than the compound of the invention in question.

Numerous synthetic routes to the compounds of the present invention can be devised by any person skilled in the art and the possible synthetic routes described below do not limit the invention. Many methods exist in the literature for the synthesis of indoles, for example: *Indoles Part One*, W. J. Houlihan (ed.), 1972; *Indoles*, Sundberg, R. J., 1996; *Heterocyclic Chemistry*, Joule, J. A.; Mills, K. 2000; *Chem. Rev.*, 2005, 105, 2873-2920; *Org. Lett.* 2006, 8, 5919-5922; *Bioorg. Med. Chem. Lett.*, 2007, 17, 902-906; US 2003/0220377; JP 2001-122855; and *Chem. Pharm. Bull.*, 2007, 55(2), 328-333. A number of possible synthetic routes are shown schematically below. Where appropriate, any initially produced compound according to the invention can be converted into another compound according to the invention by known methods.

General Method I

The following general method can be used to prepare compounds of formula (I) wherein $R^2$ is cyano, —C(NH$_2$)=NOH or —C(O)NH$_2$.

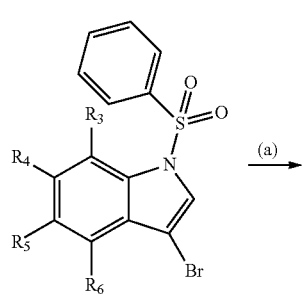

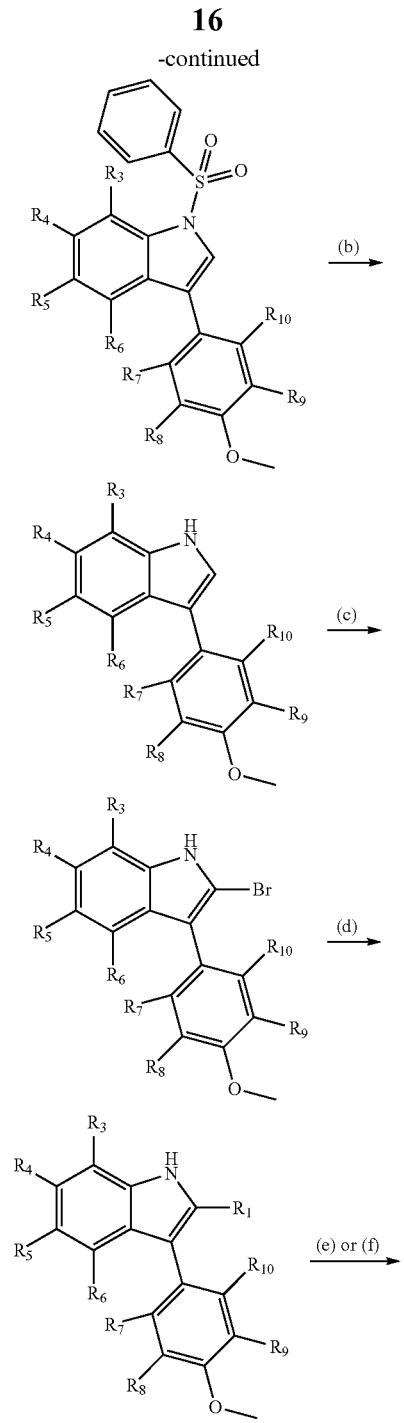

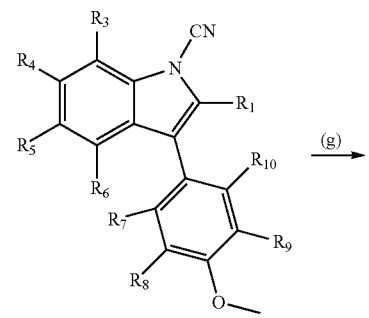

17

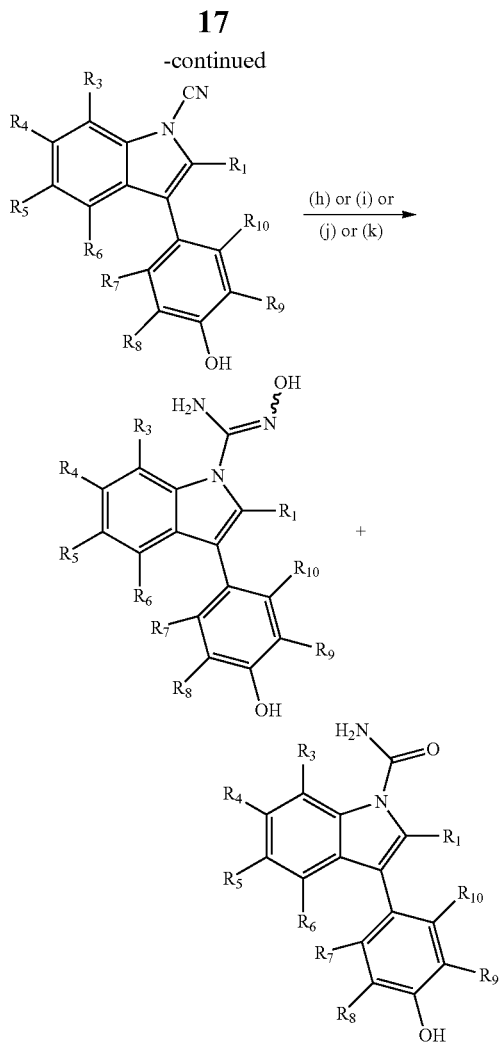

(a) 4-Methoxyphenyl boronic acid, Pd(PPh₃)₄, NaHCO₃, DME/H₂O; (b) K₂CO₃, MeOH; (c) NBS, CH₂Cl₂; (d) R₁-boronic acid, Pd(PPh₃)₄, NaHCO₃, DME/H₂O; (e) 2,2-Bis-(4-cyanatophenyl)propane, Et₃N, DMSO; (f) NaH, 2,2-Bis-(4-cyanatophenyl)propane, THF; (g) BBr₃, CH₂Cl₂; (h) Hydroxylamine hydrochloride, NaOMe, MeOH; (i) NH₂OH, DMSO; (j) NH₂OH, DCM; (k) NH₂OH, MeOH General Method I as shown in the reaction scheme above was used for the synthesis of the following Examples: 1, 2, 3, 5, 7, 10-12, and 16-23. Full experimental details of the individual steps of the general method applicable for the synthesis of the final compounds of those Examples are described in Examples 1 to 3.

General Method II

The following general method can be used to prepare compounds of formula (I) wherein $R^2$ is —SO₂N(R^C)₂.

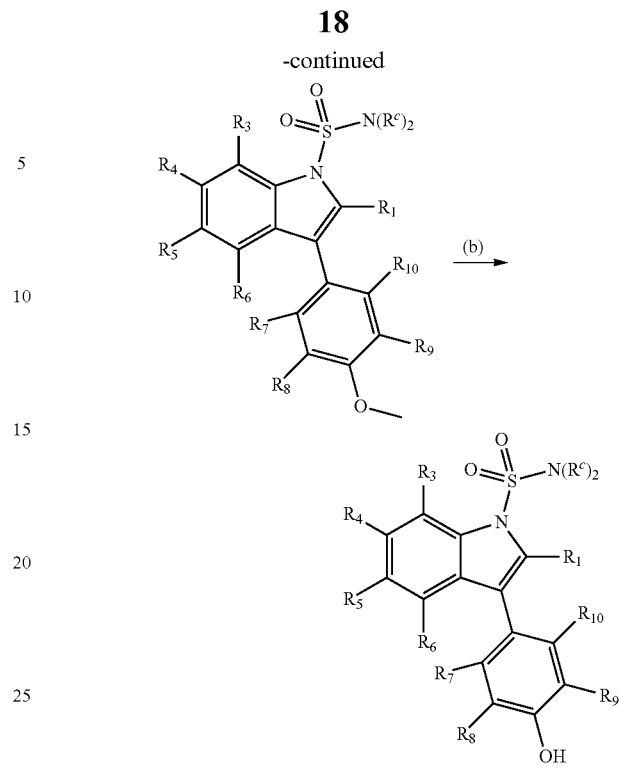

(a) (R^c)₂NSO₂Cl, NaH, DMF; (b) BF₃·SMe₂, DCM

General Method II as shown in the reaction scheme above was used for the synthesis of the following Examples: 4 and 6. Full experimental details of the individual steps of the general method applicable for the synthesis of the final compounds of those Examples are described in Example 4.

General Method III

The following general method can be used to prepare compounds of formula (I) wherein $R^2$ is CHO or —CH=NOH.

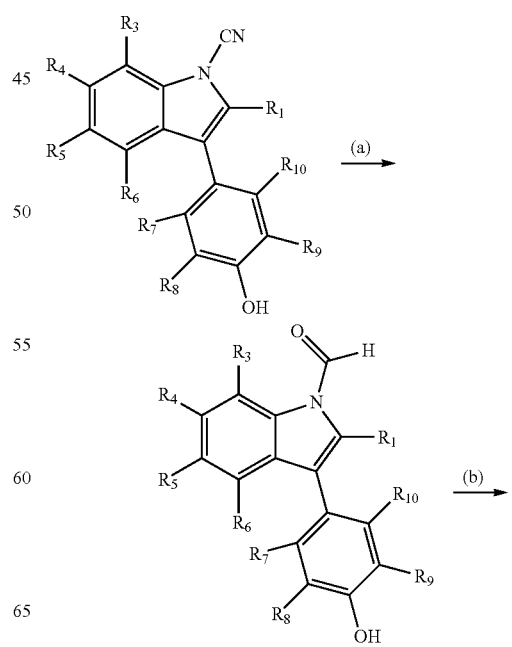

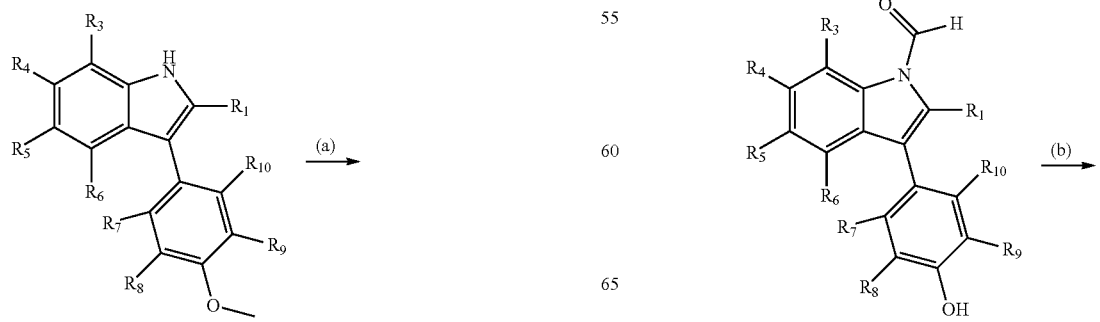

19

-continued

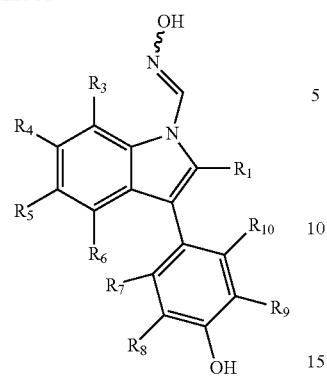

(a) DIBAH, DCM; (b) Hydroxylamine hydrochloride, pyridine, MeOH

General Method III as shown in the reaction scheme above was used for the synthesis of Example 5. Full experimental details of the individual steps of the general method applicable for the synthesis of the final compound of this Example are described in Example 5.

General Method IV

The following general method can be used to prepare compounds of formula (I) wherein $R^2$ is —C(O)NH($R^C$).

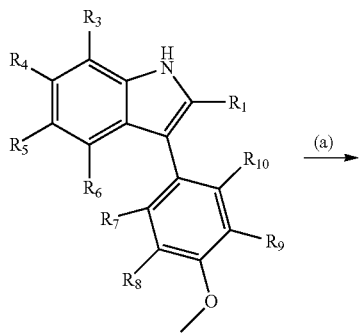

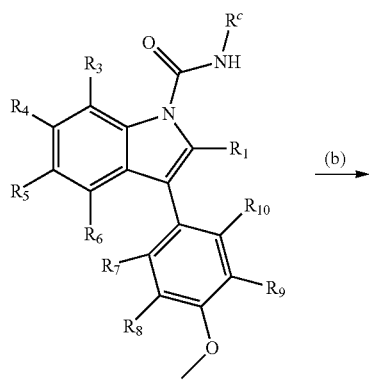

20

-continued

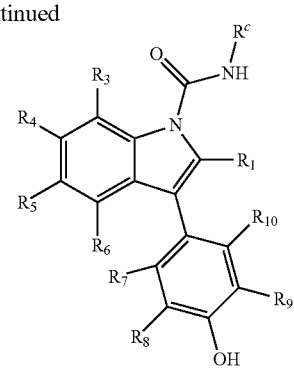

(a) NCOR$^c$, DMF; (b) BF$_3$·SMe$_2$, CH$_2$Cl$_2$

General Method IV as shown in the reaction scheme above was used for the synthesis of Examples 8, 9, 13, 14 and 15. Full experimental details of the individual steps of the general method applicable for the synthesis of the final compound of these Examples are described in Example 8.

General Method V

The following general method can be used to prepare compounds of formula (I) wherein $R^2$ is cyano, —C(NH$_2$)=NOH or —C(O)NH$_2$

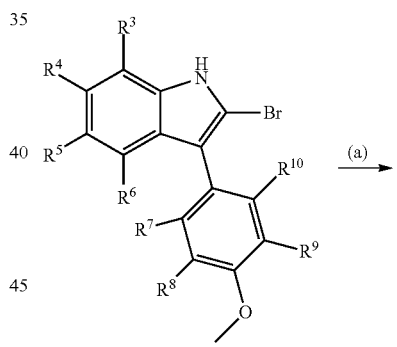

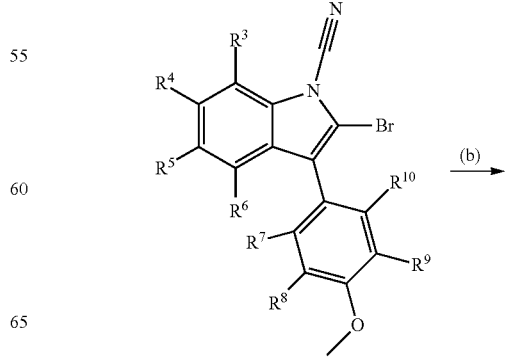

-continued

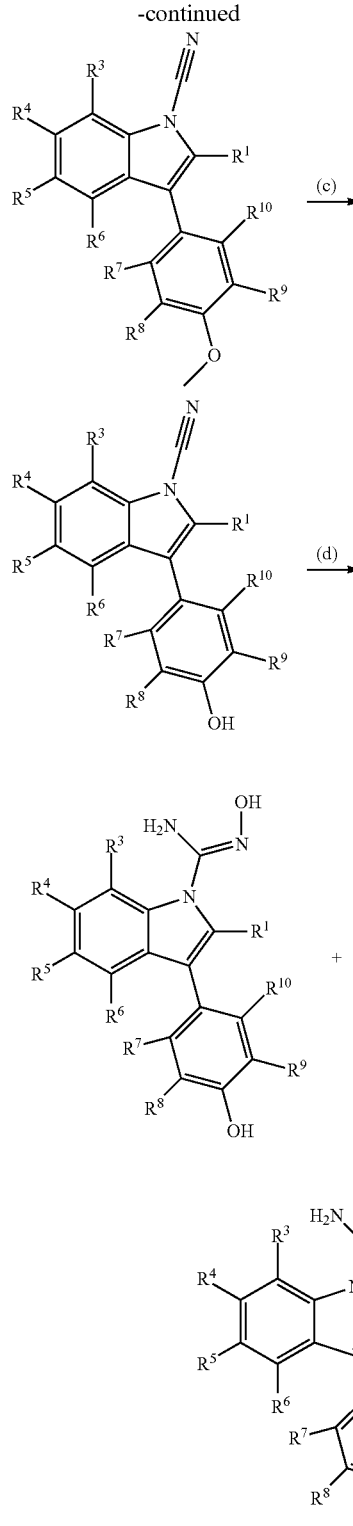

(a) NaH, 2,2-Bis-(4-cyanatophenyl)propane, THF; (b) R¹-boronic acid, Pd(PPh₃)₄, NaHCO₃, DME/H₂O; (c) BF₃•SMe₂, CH₂Cl₂; (d) NH₂OH, MeOH General Method V as shown in the reaction scheme above was used for the synthesis of Examples 24 and 25. Full experimental details of the individual steps of the general method applicable for the synthesis of the final compound of these Examples are described in Example 24 and 25.

The following Examples illustrate the invention.

EXAMPLE 1

2-(3,5-dimethylisoxazol-4-yl)-3-(4-hydroxyphenyl)-1H-indole-1-carbonitrile

Scheme 1

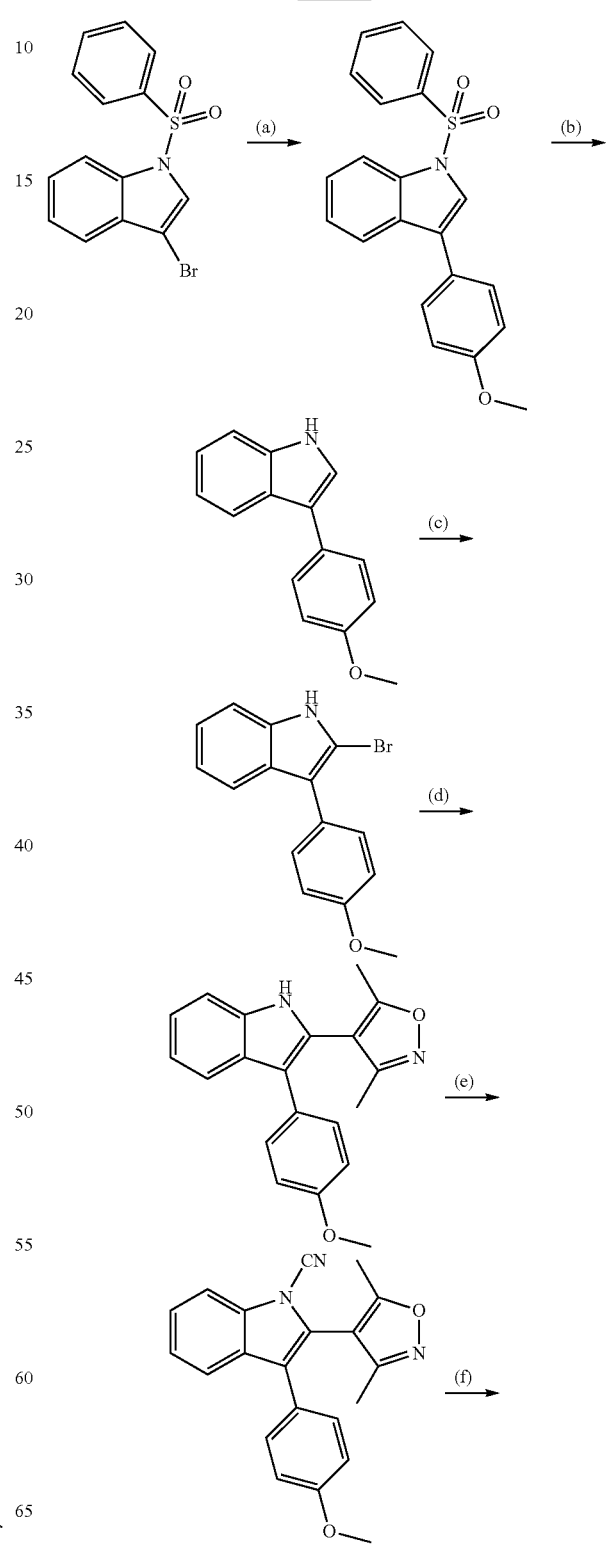

-continued

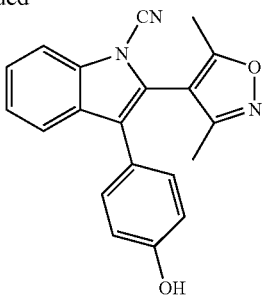

(a) 4-Methoxyphenyl boronic acid, Pd(PPh₃)₄, NaHCO₃, DME/H₂O; (b) K₂CO₃, MeOH; (c) NBS, CH₂Cl₂; (d) 3,5-dimethylisoxazol-4-boronic acid, Pd(PPh₃)₄, NaHCO₃, DME/H₂O; (e) 2,2-Bis-(4-cyanatophenyl)propane, Et₃N, DMSO; (f) BBr₃, CH₂Cl₂

Step (a): 3-bromo-1-(phenylsulfonyl)-1H-indole (500 mg, 1.49 mmol) and 5 mol % tetrakis(triphenylphosphine)palladium were mixed in 9 ml degassed DME. The mixture was stirred for 5 min under nitrogen and was then heated to 85° C. 4-Methoxyphenyl boronic acid (1.2 eq) dissolved in 3 ml DME and 5.95 ml sodium hydrogen carbonate (1 M) were simultaneously added drop wise at 85° C. over 5 min. The reaction was stirred at 85° C. for 10 min and then cooled to room temperature. DME was concentrated, water was added and the remaining aqueous mixture was extracted with DCM. The combined organic layers were concentrated and the crude product was purified on silica using EtOAc/n-heptane (1:9 to 2:8) as eluents. 363 mg 3-(4-methoxyphenyl)-1-(phenylsulfonyl)-1H-indole was obtained as white crystals.

Step (b): 3-(4-methoxyphenyl)-1-(phenylsulfonyl)-1H-indole (200 mg, 0.55 mmol) and 15 eq potassium carbonate were dissolved in 40 ml MeOH under nitrogen. The mixture was heated at reflux for 16 h, cooled to rt and then concentrated to dryness. DCM and brine were added and the mixture was acidified (pH 2-4) with 2 M HCl. The aqueous layer was extracted with DCM and the combined organic layers were concentrated. The crude product was purified on silica (EtOAc/n-Heptane, 1:1). 121.1 mg 3-(4-methoxyphenyl)-1H-indole was obtained as a white solid.

Step (c): 3-(4-methoxyphenyl)-1H-indole was dissolved in 4 ml DCM. NBS (0.9 eq) was added in small portions over 2 min. The solvent was concentrated and the crude product was purified using HPLC (MeCN/H₂O gradient). 103.3 mg 2-bromo-3-(4-methoxyphenyl)-1H-indole was obtained as a white solid.

Step (d): 2-bromo-3-(4-methoxyphenyl)-1H-indole (93 mg, 0.31 mmol), 3 mol % tetrakis(triphenylphosphine)palladium and 3,5-dimethylisoxazol-4-ylboronic acid (3 eq) were mixed in 1.5 ml degassed DME under nitrogen. 1.24 ml sodium hydrogen carbonate (1 M) was added drop wise over 5 min. The resulting mixture was stirred at 90° C. for 45 min and then cooled to rt. The solvent was evaporated under nitrogen flow and the residue was taken up in DCM. Filtering through a short plug of silica gave a crude product which was purified again on silica (EtOAc/n-Heptane 1:9-3:7). 40.5 mg 4-(3-(4-methoxyphenyl)-1H-indol-2-yl)-3,5-dimethylisoxazole was obtained as a yellow solid.

Step (e): 4-(3-(4-methoxyphenyl)-1H-indol-2-yl)-3,5-dimethylisoxazole (37 mg, 0.12 mmol) and 2,2-bis-(4-cyanatophenyl)propane (0.6 eq) were mixed in a vial. 1.8 ml DMSO and Et₃N (3 eq) were added and the mixture was heated at 120° C. in microwave. 2,2-bis-(4-cyanatophenyl) propane (5.7 eq) and Et₃N (40 eq) were added and the mixture was heated at 150° C. for 25 min in microwave. Brine was added and the aqueous layer was extracted with EtOAc 6×. The combined organic layers were dried over Na₂SO₄ and concentrated. The crude product was taken up in DCM, filtered through cotton wool and purified on silica (EtOAc/n-Heptane 1:9-2:8). 25.7 mg 2-(3,5-dimethylisoxazol-4-yl)-3-(4-methoxyphenyl)-1H-indole-1-carbonitrile was obtained as a yellowish solid.

Step (f): 2-(3,5-dimethylisoxazol-4-yl)-3-(4-methoxyphenyl)-1H-indole-1-carbonitrile was dissolved in 3 ml DCM and the mixture was cooled to −50° C. BBr₃ (5 eq) was added and the reaction was stirred at −50° C. for 4.5 h and then at −20° C. for 16 h. The mixture was cooled to −78° C. and MeOH (90 μl) was added followed by water. The aqueous layer was extracted with DCM 3× and the combined organic layers were concentrated. The crude product was purified on silica (EtOAc/n-Heptane 2:8-3:7). 4.9 mg 2-(3,5-dimethylisoxazol-4-yl)-3-(4-hydroxyphenyl)-1H-indole-1-carbonitrile was obtained as a white solid. ES/MS m/z: 330.2 (M+H), 328.3 (M−H); ¹H NMR (CDCl₃, 500 MHz): 7.75 (m, 1H), 7.67 (m, 1H), 7.51 (m, 1H), 7.41 (m, 1H), 7.20 (m, 2H), 6.88 (m, 2H), 2.28 (s, 3H) and 2.05 (s, 3H).

EXAMPLES 2 and 3

2-(3,5-dimethylisoxazol-4-yl)-N'-hydroxy-3-(4-hydroxyphenyl)-1H-indole-1-carboximidamide (E2)

2-(3,5-dimethylisoxazol-4-yl)-3-(4-hydroxyphenyl)-1H-indole-1-carboxamide (E3)

Scheme 2

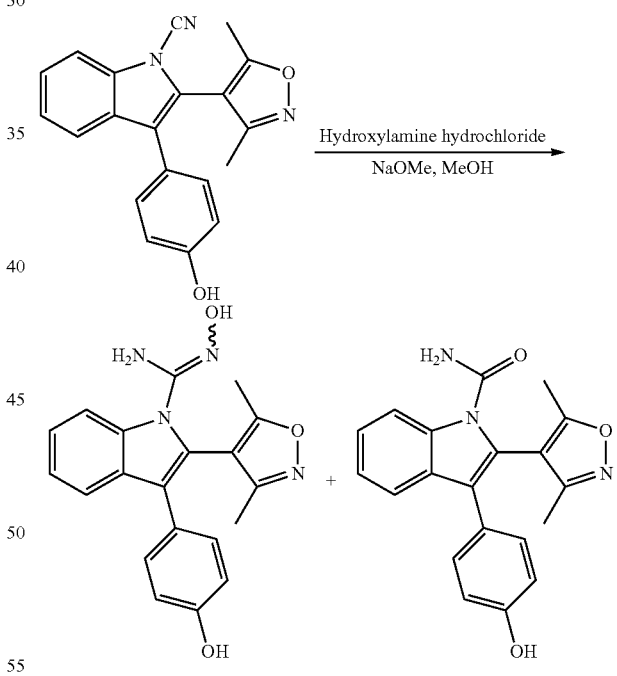

1 ml dry MeOH was added to 2-(3,5-dimethylisoxazol-4-yl)-3-(4-hydroxyphenyl)-1H-indole-1-carbonitrile (Example 1, 4.5 mg, 0.01 mmol) under nitrogen followed by 10 eq hydroxylamine hydrochloride. 10 eq NaOMe was added and the mixture was stirred for 4 h. The solvent was concentrated and the crude product was purified on silica using CH₂Cl₂/MeOH (97:3 to 96:4) as eluents. 2.10 mg 2-(3,5-dimethylisoxazol-4-yl)-N'-hydroxy-3-(4-hydroxyphenyl)-1H-indole-1-carboximidamide (E2) ES/MS m/z: 363.5 (M+H), 361.6 (M−H); ¹H NMR (MeOD, 500 MHz): 7.65 (m 1H), 7.60 (m, 1H), 7.29 (m, 1H), 7.18 (m, 1H), 7.12 (m, 2H), 6.79 (m, 2H), 2.12 (s, 3H), 1.99 (s, 3H) and 1.90 mg 2-(3,5- dimethylisoxazol-4-yl)-3-(4-hydroxyphenyl)-1H-indole-1-carboxamide (E3) ES/MS m/z: 348.2 (M+H), 346.3 (M−H); $^1$H NMR (MeOD, 500 MHz): 7.93 (m 1H), 7.61 (m, 1H), 7.35 (m, 1H), 7.23 (m, 1H), 7.08 (m, 2H), 6.81 (m, 2H), 2.07 (s, 3H), 2.03 (s, 3H) were obtained as white solids. For Example 2, the title compound was identified by $^1$H-NMR which showed that the oxime product was a single isomer, but did not confirm whether the (E) or (Z) oxime isomer had been obtained.

EXAMPLE 4

2-(3,5-dimethylisoxazol-4-yl)-3-(4-hydroxyphenyl)-N,N-dimethyl-1H-indole-1-sulfonamide (E4)

Scheme 3

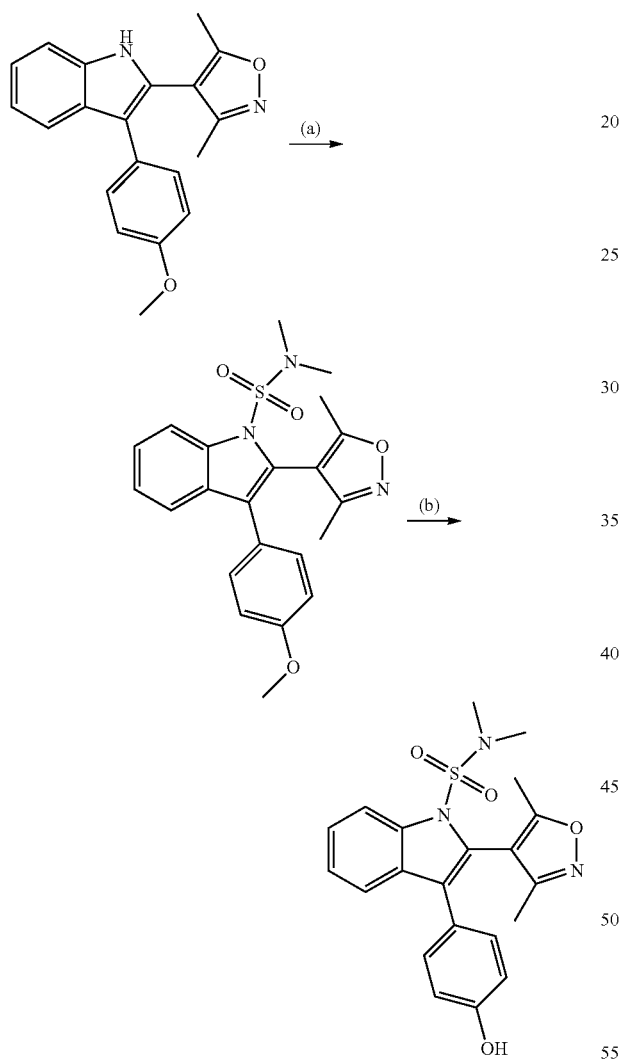

(a) $(CH_3)_2NSO_2Cl$, NaH, DMF; (b) $BF_3 \cdot SMe_2$, DCM

Step (a): 4-(3-(4-methoxyphenyl)-1H-indol-2-yl)-3,5-dimethylisoxazole (the intermediate product of step (d) from Example 1, 35 mg, 0.11 mmol) was added to a suspension of NaH (25 mg, 60% in heptane) in DMF (dry, 0.7 ml) at 0° C. under nitrogen. The mixture was stirred at rt for 30 min and was then cooled to 0° C. again. Dimethylsulfamoyl chloride (2 eq) was added drop wise. The mixture was stirred at rt for 2 h, cooled to 0° C. and water was added to quench the reaction. Extraction with DCM using isolute phase separator and concentration of the combined organic layers afforded 2-(3,5-dimethylisoxazol-4-yl)-3-(4-methoxyphenyl)-N,N-dimethyl-1H-indole-1-sulfonamide in quantitative yield.

Step (b): 2-(3,5-dimethylisoxazol-4-yl)-3-(4-methoxyphenyl)-N,N-dimethyl-1H-indole-1-sulfonamide (23 mg, 0.05 mmol) was dissolved in DCM and the mixture was cooled at 0° C. $BF_3 \cdot SMe_2$ (0.7 ml) was added drop wise and the reaction mixture was stirred in the fridge for 16 h. A few drops MeOH were added to the cool mixture. The mixture was then extracted with $H_2O$/DCM using an isolute phase separator. Concentration gave a crude product which was purified using HPLC (40-70% AcN, 25 min gradient). 5.6 mg 2-(3,5-dimethylisoxazol-4-yl)-3-(4-hydroxyphenyl)-N,N-dimethyl-1H-indole-1-sulfonamide was obtained. ES/MS m/z: 412.06 (M+H), 410.16 (M−H); $^1$H NMR (acetone-d6, 500 MHz): 8.18 (m, 1H), 7.60 (m, 1H), 7.43 (m, 1H), 7.34 (m, 1H), 7.12 (m, 2H), 6.88 (m, 2H), 2.70 (s, 6H), 2.10 (s, 3H) and 2.09 (s, 3H).

EXAMPLE 5

2-(3,5-dimethylisoxazol-4-yl)-3-(4-hydroxyphenyl)-1H-indole-1-carbaldehyde oxime (E5)

Scheme 4

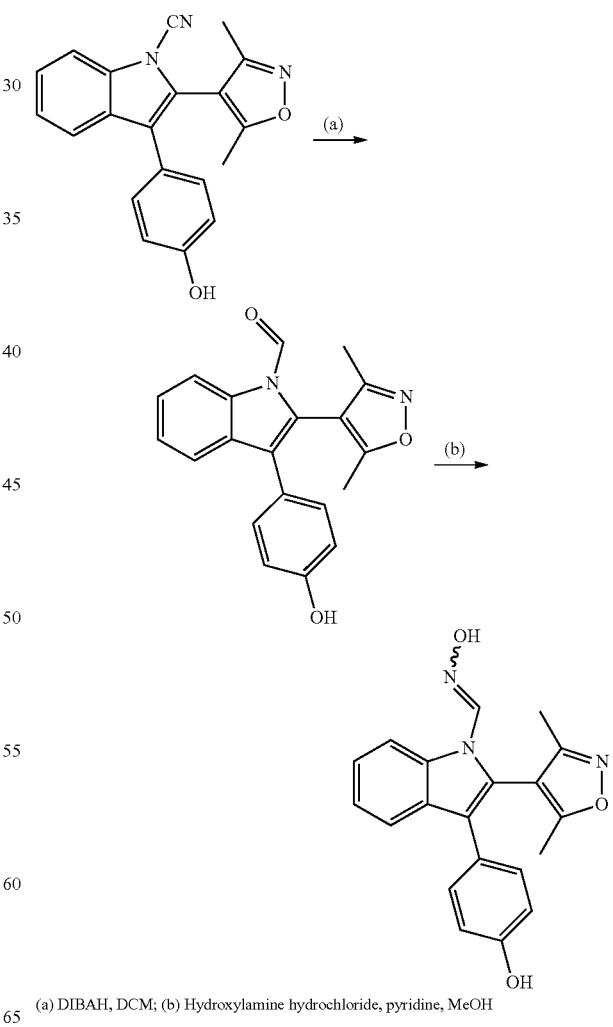

(a) DIBAH, DCM; (b) Hydroxylamine hydrochloride, pyridine, MeOH

Step (a): 2-(3,5-dimethylisoxazol-4-yl)-3-(4-hydroxyphenyl)-1H-indole-1-carbonitrile (24 mg, 0.07 mmol) was dissolved in 5 ml DCM under nitrogen and the mixture was cooled to −60° C. 5 eq DIBAH (1M in hexane) was added dropwise at −60° C. The cooling bath was removed and the reaction was stirred at rt for 16 h. 2 ml HCl (1M) was added to quench the reaction followed by 50 ml EtOAc. The resulting mixture was filtered and then washed with brine 3×. The organic layer was dried over $Na_2SO_4$ and the solvent was concentrated. 18 mg 2-(3,5-dimethylisoxazol-4-yl)-3-(4-hydroxyphenyl)-1H-indole-1-carbaldehyde was obtained.

Step (b): 2-(3,5-dimethylisoxazol-4-yl)-3-(4-hydroxyphenyl)-1H-indole-1-carbaldehyde (18 mg, 0.05 mmol) was dissolved in 5 ml MeOH. 5 eq hydroxylamine hydrochloride and 6 eq pyridine were added. The mixture was heated at reflux for 1.5 h and then allowed to cool to rt. 50 ml EtOAc were added, the resulting mixture was washed with brine 3× and then dried over $Na_2SO_4$. The solvent was concentrated and the crude product was purified using preparative HPLC. 3.5 mg 2-(3,5-dimethylisoxazol-4-yl)-3-(4-hydroxyphenyl)-1H-indole-1-carbaldehyde oxime was obtained. The title compound was identified by $^1$H-NMR which showed that the oxime product was a single isomer, but did not confirm whether the (E) or (Z) oxime isomer had been obtained. ES/MS m/z: 348.01 (M+H), 346.18 (M−H); $^1$H NMR (MeOD, 500 MHz): 8.38 (s, 1H), 8.26 (m, 1H), 7.66 (m, 1H), 7.35 (m, 1H), 7.25 (m, 1H), 7.11 (m, 2H), 6.80 (m, 2H), 2.13 (s, 3H) and 1.99 (s, 3H).

EXAMPLES 6 and 7

Example 6 was prepared using a method analogous to that used to synthesise Example 4 above, and Example 7 was prepared according to General Method I above. Full experimental details of the individual steps of the general methods are described in the Examples above. For Example 6, identification of the title compound by $^1$H-NMR showed that the oxime product was a single isomer, but did not confirm whether the (E) or (Z) oxime isomer had been obtained.

EXAMPLE 8

2-(3,5-dimethylisoxazol-4-yl)-N-ethyl-3-(4-hydroxyphenyl)-1H-indole-1-carboxamide (E8)

Scheme 5

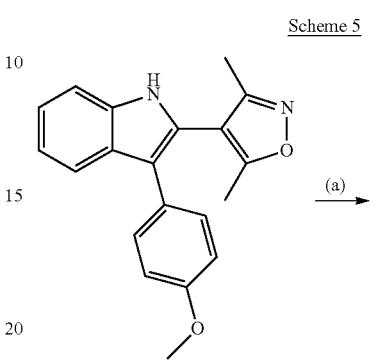

(a)

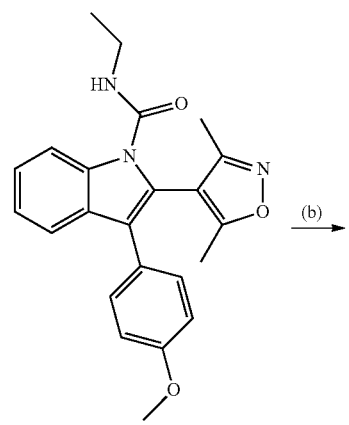

(b)

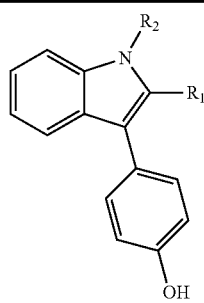

| | |
|---|---|
| E 6 | 4-(2-(3,5-dimethylisoxazol-4-yl)-1-(methylsulfonyl)-1H-indol-3-yl)phenol |

$R^1$ = 3,5-dimethylisoxazol-4-yl  $R^2$ = methylsulfonyl
ES/MS m/z: 383.04 (pos. M + H), 381.13 (neg. M − H); $^1$H NMR (acetone-d6, 500 MHz): 8.14 (m, 1H), 7.64 (m, 1H), 7.47 (m, 1H), 7.40 (m, 1H), 7.14 (m, 2H), 6.90 (m, 2H), 3.08 (s, 3H), 2.14 (s, 3H) and 2.11 (s, 3H).

| | |
|---|---|
| E 7 | 2-((E)-but-2-en-2-yl)-N'-hydroxy-3-(4-hydroxyphenyl)-1H-indole-1-carboximidamide |

$R^1$ = (Z)-but-2-en-2-yl  $R^2$ = N-Hydroxycarbamimidoyl
ES/MS m/z: 322.4 (pos. M + H), 319.6 (neg. M − H); $^1$H NMR (acetone-d6, 500 MHz): (acetone-d6, 500 MHz): 7.59 (m, 1H), 7.52 (m, 1H), 7.31 (m, 2H), 7.18 (m, 1H), 7.11 (m, 1H), 6.90 (m, 2H), 5.67 (m, 1H), 1.97 (m, 3H) and 1.37 (m, 3H).

-continued

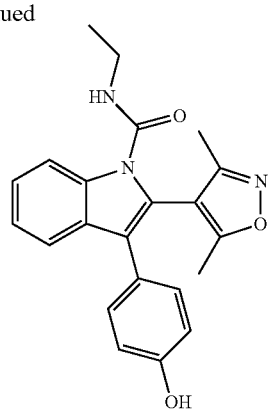

(a) EtNCO, DMF; (b) BF₃·SMe₂, CH₂Cl₂

Step (a): 4-(3-(4-methoxyphenyl)-1H-indol-2-yl)-3,5-dimethylisoxazole (15 mg, 0.06 mmol) and isocyanatoethane (40 μl) were mixed 1 ml dry DMF under nitrogen. The mixture was heated at 70° C. for 3 h. 100 μl isocyanatoethane were added and the heating at 70° C. continued over night. The crude reaction mixture was purified by prep HPLC. 8.0 mg 2-(3,5-dimethylisoxazol-4-yl)-N-ethyl-3-(4-methoxyphenyl)-1H-indole-1-carboxamide was obtained.

Step (b): 2-(3,5-dimethylisoxazol-4-yl)-N-ethyl-3-(4-methoxyphenyl)-1H-indole-1-carboxamide (8 mg, 0.02 mmol) was dissolved in 8 ml DCM and the mixture was cooled in an ice bath. BF₃.SMe₂ (0.40 ml) was added drop wise and the mixture was stirred at 0-2° C. for 16 h. A few drops MeOH were added followed by water. The layers were separated and the organic layer was concentrated. The crude product was purified by preparative HPLC. 3.4 mg 2-(3,5-dimethylisoxazol-4-yl)-N-ethyl-3-(4-hydroxyphenyl)-1H-indole-1-carboxamide was obtained. ES/MS m/z: 376.1 (pos. M+H), 374.2 (neg. M–H); ¹H NMR (acetone-d6, 500 MHz): 7.90 (m, 1H), 7.63 (m, 1H), 7.33 (m, 1H), 7.23 (m, 1H), 7.14 (m, 2H), 6.88 (m, 2H), 3.38 (m, 2H), 2.04 (s, 3H), 2.03 (s, 3H) and 1.16 (t, 3H, J=7.3 Hz).

EXAMPLES 9-15

Examples 9, 13, 14 and 15 were prepared according to General Method IV above, and Examples 10-12 were prepared according to General Method I above. Full experimental details of the individual steps of the general methods are described in the Examples above. For Examples 10 and 12, identification of the title compound by ¹H-NMR showed that the oxime product was a single isomer, but did not confirm whether the (E) or (Z) oxime isomer had been obtained.

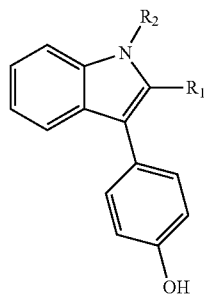

E 9  2-(3,5-dimethylisoxazol-4-yl)-3-(4-hydroxyphenyl)-N-methyl-1H-indole-1-carboxamide
$R^1$ = 3,5-dimethylisoxazol-4-yl  $R^2$ = N-methyl carbamoyl
ES/MS m/z: 362.1 (pos. M + H), 360.15 (neg. M – H); ¹H NMR (acetone-d6, 500 MHz): (acetone-d6, 500 MHz): 7.91 (m, 1H), 7.63 (m, 1H), 7.33 (m, 1H), 7.23 (m, 1H), 7.13 (m, 2H), 6.88 (m, 2H), 2.91 (s, 3H) and 2.02 (s, 6H).

E 10  2-(2,4-dimethylthiophen-3-yl)-N'-hydroxy-3-(4-hydroxyphenyl)-1H-indole-1-carboximidamide
$R^1$ = 2,4-dimethylthiophen-3-yl  $R^2$ = N-Hydroxycarbamimidoyl
ES/MS m/z: 378.5 (pos. M + H), 376.0 (neg. M – H); ¹H NMR (MeOD, 500 MHz): 7.68 (m, 1H), 7.59 (m, 1H), 7.24 (m, 1H), 7.15 (m, 1H), 7.07 (m, 2H), 6.75 (s, 1H), 6.70 (m, 2H), 2.14 (s, 3H) and 1.95 (s, 3H).

E 11  2-(2,4-dimethylthiophen-3-yl)-3-(4-hydroxyphenyl)-1H-indole-1-carboxamide
$R^1$ = 2,4-dimethylthiophen-3-yl  $R^2$ = carbamoyl
ES/MS m/z: 363.5 (pos. M + H), 361 (neg. M – H); ¹H NMR (MeOD, 500 MHz): 8.23 (m, 1H), 7.62 (m, 1H), 7.32 (m, 1H), 7.23 (m, 1H), 7.00 (m, 2H), 6.94 (s, 1H), 6.72 (m, 2H), 2.07 (s, 3H) and 2.00 (s, 3H).

E 12  2-(2,6-dimethylphenyl)-N'-hydroxy-3-(4-hydroxyphenyl)-1H-indole-1-carboximidamide
$R^1$ = 2,6-dimethylphenyl  $R^2$ = N-Hydroxycarbamimidoyl
ES/MS m/z: 372.2 (pos. M + H), 370.2 (neg. M – H); ¹H NMR (acetone-d6, 500 MHz): 7.71 (m, 1H), 7.57 (m, 1H), 7.24 (m, 1H), 7.17 (m, 1H), 7.15 (m, 1H), 7.09 (m, 2H), 7.02 (m, 2H), 6.74 (m, 2H) and 2.09 (s, 6H).

E 13  2-(3,5-dimethylisoxazol-4-yl)-3-(4-hydroxyphenyl)-N-isopropyl-1H-indole-1-carboxamide
$R^1$ = 3,5-dimethylisoxazol-4-yl  $R^2$ = N-isopropyl carbamoyl
ES/MS m/z: 389.2 (pos. M + H), 388.2 (neg. M – H); ¹H NMR (acetone-d6, 500 MHz); 7.85 (m, 1H), 7.64 (m, 1H), 7.33 (m, 1H), 7.22 (m, 1H), 7.14 (m, 2H), 6.88 (m, 2H), 4.03 (m, 1H), 2.06 (s, 3H), 2.03 (s, 3H), 1.21 (d, 3H, J = 6.6 Hz) and 1.18 (t, 3H, J = 6.6 Hz).

E 14  2-(3,5-dimethylisoxazol-4-yl)-3-(4-hydroxyphenyl)-N-pentyl-1H-indole-1-carboxamide
$R^1$ = 3,5-dimethylisoxazol-4-yl  $R^2$ = N-pentyl carbamoyl
ES/MS m/z: 418.2 (pos. M + H), 416.2 (neg. M – H); ¹H NMR (acetone-d6, 500 MHz); 7.88 (m, 1H), 7.63 (m, 1H), 7.33 (m, 1H), 7.23 (m, 1H), 7.14 (m, 2H), 6.88 (m ,2H), 3.34 (m, 2H), 2.05 (s, 3H), 2.03 (s, 3H), 1.56 (m, 2H), 1.36-1.25 (m, 4H) and 0.90 (t, 3H, J = 7.3 Hz).

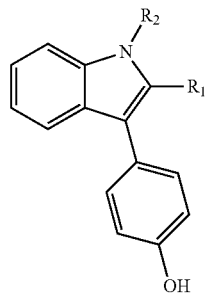

E 15  2-(2,4-dimethylthiophen-3-yl)-N-ethyl-3-(4-hydroxyphenyl)-1H-indole-1-carboxamide
$R^1$ = 2,4-dimethylthiophen-3-yl  $R^2$ = carbamoyl
ES/MS m/z: 391.1 (pos. M + H), 389.1 (neg. M − H); $^1$H NMR (acetone-d6, 500 MHz): 8.19 (m, 1H),
7.66 (m, 1H), 7.32 (m, 1H), 7.23 (m, 1H), 7.08 (m, 2H), 7.02 (s, 1H), 6.82 (m, 2H), 3.28 (m, 1H), 3.19
(m, 1H), 2.09 (s, 3H), 1.99 (s, 3H) and 0.96 (t, 3H, J = 7.3 Hz).

EXAMPLES 16-20

Examples 16-20 were prepared according to General Method I above. Full experimental details of the individual steps of the general methods are described in the Examples above. For each of Examples 16-20, identification of the title compound by $^1$H-NMR showed that the oxime product was a single isomer, but did not confirm whether the (E) or (Z) oxime isomer had been obtained.

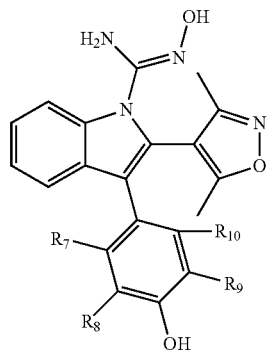

E 16  3-(3,5-difluoro-4-hydroxyphenyl)-2-(3,5-dimethylisoxazol-4-yl)-N'-hydroxy-1H-indole-1-carboximidamide
$R^7$ = H  $R^8$ = F  $R^9$ = F  $R^{10}$ = H
ES/MS m/z: 399.05 (pos. M + H), 397.15 (neg. M − H); $^1$H NMR (MeOD, 500 MHz): 7.67 (d, 1H,
J = 8.0 Hz), 7.61 (d, 1H, J = 8.1 Hz), 7.32 (t, 1H, J = 8.1 Hz), 7.23 (t, 1H, J = 8.0 Hz), 6.86-6.79 (m, 2H), 2.21
(s, 3H) and 2.01 (s, 3H).
E 17  3-(2,3-difluroo-4-hydroxyphenyl)-2-(3,5-dimethylisoxazol-4-yl)-N'-hydroxy-1H-indole-1-carboximidamide
$R^7$ = F  $R^8$ = F  $R^9$ = H  $R^{10}$ = H
ES/MS m/z: 399.05 (pos. M + H), 397.17 (neg. M − H); $^1$H NMR (MeOD, 500 MHz): 7.62 (d, 1H,
J = 8.3 Hz), 7.45 (d, 1H, J = 7.8 Hz), 7.31 (m, 1H), 7.19 (m, 1H), 6.89 (m, 1H), 6.76 (m, 1H'), 2.16 (s, 3H)
and 2.06 (s, 3H).
E 18  2-(3,5-dimethylisoxazol-4-yl)-3-(2-fluoro-4-hydroxyphenyl)-N'-hydroxy-1H-indole-1-carboximidamide
$R^7$ = F  $R^8$ = H  $R^9$ = H  $R^{10}$ = H
ES/MS m/z: 381.14 (pos. M + H), 379.1 (neg. M − H); $^1$H NMR (MeOD, 500 MHz): 7.61 (m, 1H), 7.44
(m, 1H), 7.29 (m, 1H), 7.16 (m, 1H), 7.08 (t, 1H, J = 8.5 Hz), 6.63 (dd, 1H, J = 8.5, 2.4 Hz), 6.55 (dd, 1H,
J = 11.7, 2.4 Hz), 2.14 (s, 3H) and 2.05 (s, 3H).
E 19  3-(2,5-difluoro-4-hydroxyphenyl)-2-(3,5-dimethylisoxazol-4-yl)-N'-hydroxy-1H-indole-1-carboximidamide
$R^7$ = F  $R^8$ = H  $R^9$ = F  $R^{10}$ = H
ES/MS m/z: 399.08 (pos. M + H), 397.14 (neg. M − H); $^1$H NMR (MeOD, 500 MHz): 7.61 (m, 1H),
7.47 (m, 1H), 7.30 (m, 1H), 7.19 (m, 1H), 6.97 (dd, 1H, J = 11.2, 6.7 Hz), 6.70 (dd, 1H, J = 10.6, 7.3 Hz),
2.17 (s, 3H) and 2.06 (s, 3H).
E 20  2-(3,5-dimethylisoxazol-4-yl)-3-(3-fluoro-4-hydroxyphenyl)-N'-hydroxy-1H-indole-1-carboximidamide
$R^7$ = H  $R^8$ = F  $R^9$ = H  $R^{10}$ = H
ES/MS m/z: 381.07 (pos. M + H), 379.2 (neg. M − H); $^1$H NMR (MeOD, 500 MHz): 7.66 (m, 1H), 7.60
(m, 1H), 7.31 (m, 1H), 7.20 (m, 1H), 7.02-6.92 (m, 3H), 2.19 (s, 3H) and 2.00 (s, 3H).

EXAMPLE 21

5-chloro-2-(2,4-dimethylthiophen-3-yl)-N'-hydroxy-3-(4-hydroxyphenyl)-1H-indole-1-carboximidamide (E21)

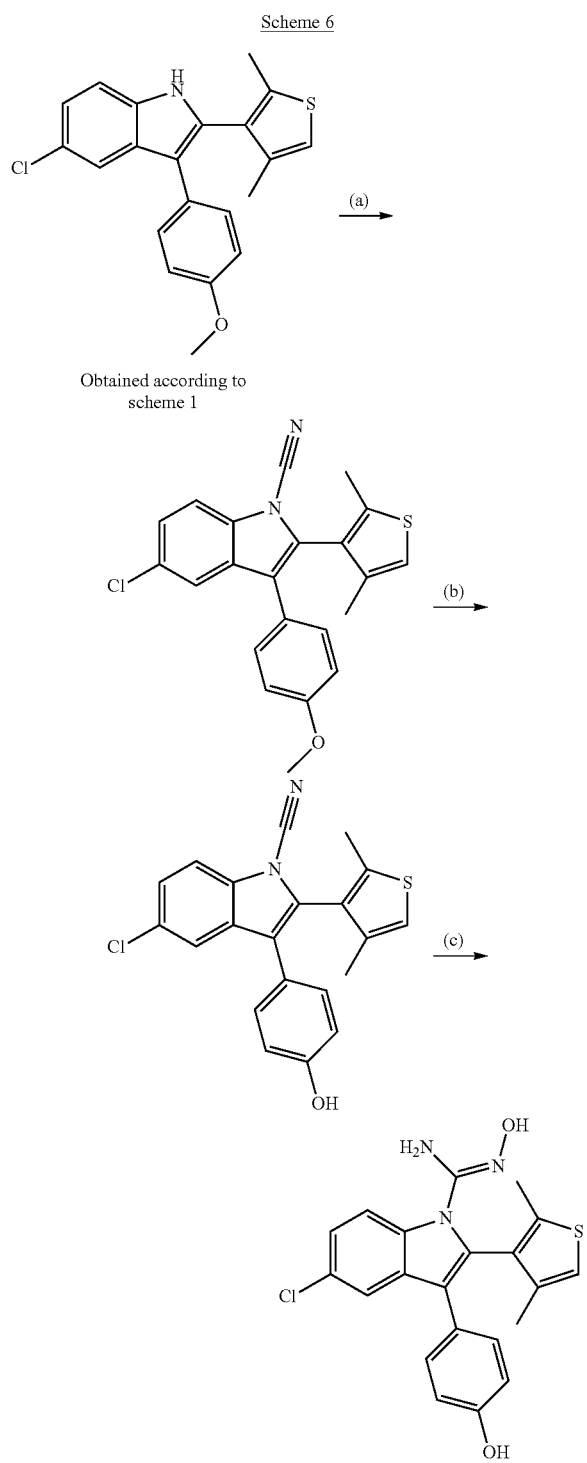

(a) NaH, 2,2-Bis-(4-cyanatophenyl)propane, THF (b) BF₃•SMe₂, DCM (c) NH₂OH, DCM

Step (a): NaH (6.11 mg, 0.25 mmol) was stirred in dry THF (1 ml) at 0° C. and 5-chloro-2-(2,4-dimethylthiophen-3-yl)-3-(4-methoxyphenyl)-1H-indole (72 mg, 0.20 mmol) dissolved in dry THF (2 ml) was added dropwise and the mixture was stirred at 0° C. for 5 min. 2,2-bis-(4-cyanatophenyl)propane (70.8 mg, 0.25 mmol) dissolved in dry THF (2 ml) was added dropwise and the mixture was stirred at room temperature for 9 h. NH₄Cl (aq, sat) was added followed by brine and the aqueous mixture was extracted with DCM. The solvent was concentrated and the crude product was purified on silica (EtOAc/n-Heptane 1:9). 72 mg 5-chloro-2-(2,4-dimethylthiophen-3-yl)-3-(4-methoxyphenyl)-1'-1-indole-1-carbonitrile was obtained.

Step (b): 5-chloro-2-(2,4-dimethylthiophen-3-yl)-3-(4-methoxyphenyl)-1H-indole-1-carbonitrile (75 mg, 0.19 mmol) was dissolved in 4 ml DCM and the mixture was cooled in an ice bath. BF₃.SMe₂ (0.20 ml, 1.91 mmol) was added drop wise and the mixture was stirred at room temperature for 24 h. A few drops MeOH were added at 0° C. followed by NaHCO₃ (aq, sat) and brine. The layers were separated and the organic layer was concentrated. The crude product was purified on silica (MeOH/DCM 1:99). 42.0 mg 5-chloro-2-(2,4-dimethylthiophen-3-yl)-3-(4-hydroxyphenyl)-1H-indole-1-carbonitrile was obtained.

Step (c): Hydroxylamine (16.3 M solution in water, 0.69 mL, 11.0 mmol) was added to 5-chloro-2-(2,4-dimethylthiophen-3-yl)-3-(4-hydroxyphenyl)-1H-indole-1-carbonitrile (42 mg, 0.11 mmol) in DCM (5 mL) at 0° C. and the reaction was stirred at 0° C. for 65 h. Brine was added and the aqueous mixture was extracted with DCM. The solvent was concentrated and the crude product was purified by preparative HPLC to give 5-chloro-2-(2,4-dimethylthiophen-3-yl)-N'-hydroxy-3-(4-hydroxyphenyl)-1H-indole-1-carboximidamide (7.0 mg, 35%). Identification of the title compound by ¹H-NMR showed that the oxime product was a single isomer, but did not confirm whether the (E) or (Z) oxime isomer had been obtained. ES/MS m/z: 414.5; 412.4 (M+H), 412.3; 409.9 (M−H); ¹H NMR (acetone-d6, 500 MHz): 7.65 (d, 1H, J=2.1 Hz), 7.58 (d, 1H, J=8.8 Hz), 7.25 (dd, 1H, J=8.8, 2.1 Hz), 7.10 (m, 2H), 6.83-6.80 (m, 3H), 2.18 (s, 3H) and 1.95 (d, 3H, J=1.1 Hz).

EXAMPLES 22 and 23

Examples 22 and 23 were prepared according to General Method I above. Full experimental details of the individual steps of the general methods are described in Example 1 and 21 above. For each of Examples 22 and 23, identification of the title compounds by ¹H-NMR showed that the oxime product was a single isomer, but did not confirm whether the (E) or (Z) oxime isomer had been obtained.

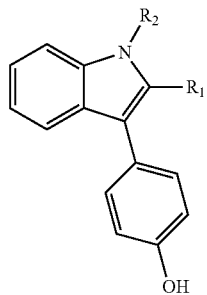

| | |
|---|---|
| E 22 | 5-chloro-2-(3,5-dimethylisoxazol-4-yl)-N'-hydroxy-3-(4-hydroxyphenyl)-1H-indole-1-carboximidamide |

$R^1$ = 3,5-dimethylisoxazol-4-yl  $R^2$ = N-Hydroxycarbamimidoyl
ES/MS m/z: 399.2; 397.4 (pos. M + H), 397; 394.9 (neg. M – H); $^1$H NMR (acetone-d6, 500 MHz): 7.62 (d, 1H, J = 2.1 Hz), 7.59 (d, 1H, J = 8.7 Hz), 7.28 (dd, 1H, J = 8.7, 2.1 Hz), 7.16 (m, 2H), 6.88 (m, 2H), 2.18 (s, 3H) and 1.97 (s, 3H).

| | |
|---|---|
| E 23 | 2-(2,4-dimethylfuran-3-yl)-N'-hydroxy-3-(4-hydroxyphenyl)-1H-indole-1-carboximidamide |

$R^1$ = 2,4-dimethylfuran-3-yl  $R^2$ = N-Hydroxycarbamimidoyl
ES/MS m/z: 360.1 (neg. M – H); $^1$H NMR (acetone-d6, 500 MHz): 7.62 (d, 1H, J = 2.1 Hz), 7.59 (d, 1H, J = 8.7 Hz), 7.28 (dd, 1H, J = 8.7, 2.1 Hz), 7.16 (m, 2H), 6.88 (m, 2H), 2.18 (s, 3H) and 1.97 (s, 3H).

EXAMPLE 24 and 25

2-(3,5-dimethylisothiazol-4-yl)-N'-hydroxy-3-(4-hydroxyphenyl)-1H-indole-1-carboximidamide (E24)

2-(3,5-dimethylisothiazol-4-yl)-3-(4-hydroxyphenyl)-1H-indole-1-carboxamide (E25)

Scheme 7

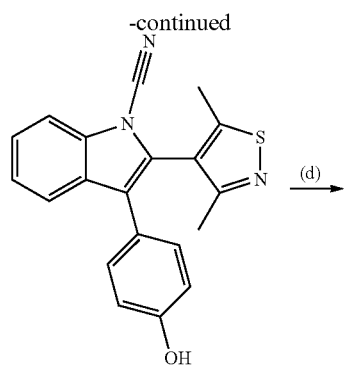

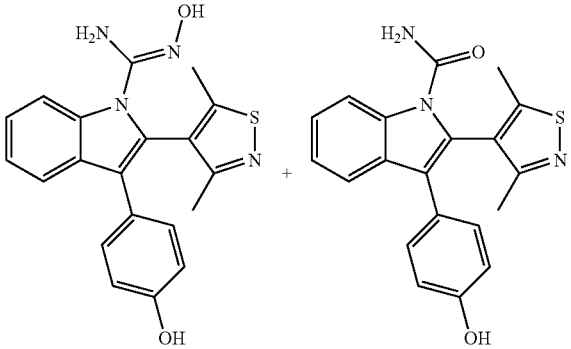

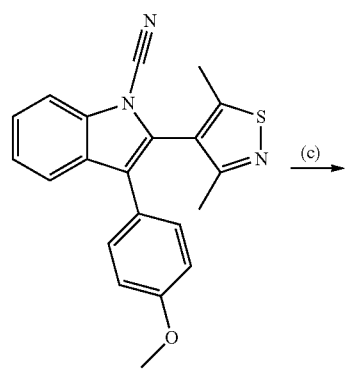

(a) NaH, 2,2-Bis-(4-cyanatophenyl)propane, THF; (b) 3,5-dimethylisothiazol-4-ylboronic acid, Pd(PPh$_3$)$_4$, NaHCO$_3$, DME/H$_2$O; (c) BF$_3$•SMe$_2$, CH$_2$Cl$_2$; (d) NH$_2$OH, MeOH Step (a): NaH (18.35 mg, 0.76 mmol) was stirred in dry THF (1 ml) at 0° C. and 2-bromo-3-(4-methoxyphenyl)-1H-indole (210 mg, 0.69 mmol) dissolved in dry THF (4.5 ml) was added dropwise. The mixture was stirred at 0° C. for 5 min and then 2,2-bis-(4-cyanatophenyl)propane (251 mg, 0.90 mmol) dissolved in dry THF (4.5 ml) was added dropwise. Water was added and this mixture was stirred for 30 min Brine was added and the aqueous mixture was extracted with DCM. The solvent was concentrated and the crude product was purified on silica (EtOAc/n-Heptane 1:4). 198 mg 2-bromo-3-(4-methoxyphenyl)-1H-indole-1-carbonitrile was obtained.

Step (b): 2-bromo-3-(4-methoxyphenyl)-1H-indole-1-carbonitrile (70.0 mg, 0.21 mmol), tetrakis(triphenylphosphine)palladium (24.7 mg, 0.21 mmol) and 3,5-dimethylisothiazol-4-ylboronic acid (102.3 mg, 0.43 mmol) were mixed in 3.5 ml DME and 0.86 ml sodium hydrogen carbonate (1 M) under nitrogen. The resulting mixture was heated at 120° C. for 20 min in microwave. The solvent was evaporated and the residue was dissolved in DCM. Filtering through a short plug of silica gave a crude product which was purified on silica (EtOAc/n-Heptane 1:4). 38.0 mg 2-(3,5-dimethylisothiazol-4-yl)-3-(4-methoxyphenyl)-1H-indole-1-carbonitrile was obtained.

Step (c): 2-(3,5-dimethylisothiazol-4-yl)-3-(4-methoxyphenyl)-1H-indole-1-carbonitrile (38 mg, 0.11 mmol) was dissolved in 10 ml DCM and the mixture was cooled in an ice bath. $BF_3.SMe_2$ (0.56 ml, 5.29 mmol) was added drop wise and the mixture was stirred at 0-2° C. for 16 h. A few drops MeOH were added followed by $NaHCO_3$ (aq, sat). The layers were separated and the organic layer was concentrated. The crude product was purified by preparative HPLC. 18.0 mg 2-(3,5-dimethylisothiazol-4-yl)-3-(4-hydroxyphenyl)-1H-indole-1-carbonitrile was obtained.

Step (d): Hydroxylamine (16.3 M solution in water, 0.33 mL, 5.21 mmol) was added to 2-(3,5-dimethylisothiazol-4-yl)-3-(4-hydroxyphenyl)-1H-indole-1-carbonitrile (18 mg, 0.05 mmol) in MeOH (2 mL) and the reaction was stirred at 130° C. for 20 min in the microwave. The mixture was purified by preparative HPLC to give E24 2-(3,5-dimethylisothiazol-4-yl)-N'-hydroxy-3-(4-hydroxyphenyl)-1H-indole-1-carboximidamide (7.0 mg, 35%); ES/MS m/z 379.11 (M+H), 377.14 (M−H); $^1$H NMR (acetone-d6, 500 MHz): 7.70 (dd, 1H, J=7.9, 1.0 Hz), 7.59 (dd, 1H, J=9.0, 0.9 Hz), 7.29 (m, 1H), 7.20 (m, 1H), 7.09 (m, 2H), 6.81 (m, 2H), 2.30 (s, 3H) and 2.16 (s, 3H) and E25 2-(3,5-dimethylisothiazol-4-yl)-3-(4-hydroxyphenyl)-1H-indole-1-carboxamide (5 mg, 26%), ES/MS m/z 364.11 (M+H), 362.14 (M−H); $^1$H NMR (acetone-d6, 500 MHz): 8.12 (d, 1H, J=8.4 Hz), 7.67 (d, 1H, J=7.9 Hz), 7.36 (m, 1H), 7.26 (m, 1H), 7.05 (m, 2H), 6.83 (m, 2H) and 2.21 (s, 6H). For each of the title compounds, identification by $^1$H-NMR showed that the amide oxime product was a single isomer, but did not confirm whether the (E) or (Z) oxime isomer had been obtained.

Binding Assay 1: Estrogen Receptor Binding Assay

The estrogen receptor ligand binding assays are designed as scintillation proximity assays (SPA), employing the use of tritiated estradiol ($^3$H-E2) and recombinant expressed biotinylated estrogen receptor binding domains. The binding domains of human ERα (ERα-LBD, pET-N-AT #1, aa 301-595) and ERβ (ERβ-LBD, pET-N-AT #1, aa 255-530) proteins are produced in E. coli ((BL21, (DE3), pBirA)) at 22 C in 2×LB medium supplemented with 50 uM biotin. After 3 h of IPTG induction (0.55 mM), cells are harvested by centrifugation at 7300×g for 15 min and cell pellets stored frozen in −20 C. Extraction of ERα and ERβ are performed using 5 g of cells suspended in 50 mL of extraction buffer (50 mM Tris, pH 8.0, 100 mM KCl, 4 mM EDTA, 4 mM DDT and 0.1 mM PMSF). The cell suspension is run twice through a Microfluidizer M-110L (Microfluidics) and centrifuged at 15,000×g for 60 min. The supernatant is aliquoted and stored in −70 C.

Dilute ERα-LBD or ERβ-LBD extracts in assay buffer (18 mM $K_2HPO_4$, 2 mM $KH_2PO_4$, 20 mM $Na_2MoO_4$, 1 mM EDTA, 1 mM TCEP) 1:676 and 1:517 for alpha and beta respectively. The diluted receptor concentrations should be 900 fmol/L. Preincubate the extracts with streptavidin coated polyvinyltoluene SPA beads (RPNQ0007, GE Healthcare) at a concentration of 0.43 mg/mL for 1 hr at room temperature.

Test compounds are evaluated over a range of concentrations from 157 µM to 37.5 µM. The test compound stock solutions should be made in 100% DMSO at 5× of the final concentration desired for testing in the assay. The amount of DMSO in the test wells of the 384 well plate will be 20%. Add 18 µl aliquots of test compounds to the assay plates followed by 35 µl of the preincubated receptor/SPA bead mix and finally add 35 µl of 3 nM $^3$H-E2. Cover the plates with a plastic sealer, centrifuge for 1 minute at 1000 rpm and equilibrate over night on a shaker at room temperature. The following morning, centrifuge the plates 5 minutes at 2000 rpm and measure on a plate scintillation counter e.g. a PerkinElmer Microbeta 1450 Trilux.

For compounds able to displace 3[H]-E2 from the receptor an $IC_{50}$-value (the concentration required to inhibit 50% of the binding of 3[H]-E2) is determined by a non-linear four parameter logistic model; b=((bmax−bmin)/(1+(I/$IC_{50}$)S))+bmin I is added concentration of binding inhibitor, $IC_{50}$ is the concentration of inhibitor at half maximal binding and S is a slope factor. The Microbeta-instrument generates the mean cpm (counts per minute) value/minute and corrects for individual variations between the detectors thus generating corrected cpm values.

Transactivation Assay 1: Transactivation Assay in Human Embryonic Kidney 293 Cells Stably Transfected with pERE-ALP and Human Estrogen Receptor Alpha The expression vector pMThERα contains an insert of wild type human estrogen receptor alpha with deleted leader. The pERE-ALP reporter construct contains the gene for the secreted form of placental alkaline phosphatase (ALP) and the vitellogenin estrogen response element (ERE). The human embryonic kidney 293 cells are transfected in two steps. Firstly, a stable clone mix transfected with the pERE-ALP reporter gene construct and pSV2-Neo for selection is developed. Secondly, the stable clone mix is transfected with pMThERα and a pKSV-Hyg resistance vector for selection. All transfections are performed using Lipofectamine (Invitrogen) according to supplier's recommendations. A selected clone with both pERE-ALP and pMThERα is used for the transactivation assay.

The cells are seeded in 384-well plates at 12 500 cells per well in Ham's F12 Coon's modification (without phenol red) with 10% dextran-coated charcoal treated (DCC) fetal bovine serum (FBS), 2 mM L-glutamine and 50 µg/ml gentamicin. After 24 h incubation (37° C., 5% $CO_2$) the seeding medium is discarded and replaced with 20 µl Ham's F12 Coon's modification (without phenol red) with 1.5% DCC-FCS, 2 mM L-glutamine and supplemented with 100 U/ml penicillin and 100 µg/ml streptomycin. The selected compounds are added to the wells in 12 concentrations ranging from 3.3 pM to 33 µM. The compounds are dissolved in 100% dimethylsulphoxide (DMSO) and the final concentration of DMSO in the assay is 0.1%. After 72 h incubation (37° C., 5% $CO_2$) the medium is assayed for ALP activity by a chemiluminescence assay; a 10 µl aliquot of the cell culture medium is mixed with 100 µl assay buffer (0.1 M diethanolamine, 1 mM $MgCl_2$) and 0.5 mM disodium 3-(4-methoxyspiro 1,2-dioxetane-3,2'-(5'-chloro)-tricyclo[3.3.1.13,7]decan-4-yl)phenyl phosphate (CSPD) (Tropix, Applied Biosystems) and incubated for 20 min at 37° C. and 15 min at room temperature before measurement chemiluminescent light signal (one second per well) in a Wallac Microbeta Trilux 1450-028 (PerkinElmer). The half maximal effective concentrations ($EC_{50}$) are calculated from the curves fitted to the concentration-response data with a four parameter logistic model in XLfit software version 2.0 (IDBS) or later.

Transactivation Assay 2: Transactivation Assay in Human Embryonic Kidney 293 Cells Stably Transfected with pERE2-ALP and Human Estrogen Receptor Beta Generation of stable HEK293 cell lines (CRL-1573; American Type Culture Collection) expressing the reporter vector pERE2-ALP and human estrogen receptor beta (hERβ 530) have been described (Mol Pharmacol 1998, 54, 105-112; Endocrinology 2002, 143, 1558-1561).

The cells were seeded in 384-well plates at 12 500 cells per well in Ham's F12 Coon's modification (without phenol red) with 10% dextran-coated charcoal treated (DCC) fetal bovine serum (FBS), 2 mM L-glutamine and 50 µg/ml gentamicin. After 24 h incubation (37° C., 5% CO2) the seeding medium was discarded and replaced with 20 µl Ham's F12 Coon's modification (without phenol red) with 1.5% DCC-FCS, 2 mM L-glutamine and supplemented with 100 U/ml penicillin and 100 µg/ml streptomycin. The selected compounds were added to the wells in 12 concentrations ranging from 3.3 µM to 33 µM. The compounds were dissolved in 100% dimethylsulfoxide (DMSO) and the final concentration of DMSO in the assay was 0.1%. After 72 h incubation (37° C., 5% CO2) the medium was assayed for ALP activity by a chemiluminescence assay; a 10 µl aliquot of the conditioned medium was mixed with 100 µl assay buffer (0.1 M diethanolamine, 1 mM MgC12) and 0.5 mM disodium 3-(4-methoxyspiro 1,2-dioxetane-3,2'-(5'-chloro)-tricyclo[3.3.1.13,7]decan-4-yl) phenyl phosphate (CSPD) (Tropix, Applied Biosystems) and incubated for 20 min at 37° C. and 15 min at room temperature before measurement of the chemiluminescent signal (one second per well) in a Wallac Microbeta Trilux 1450-028 (PerkinElmer). The ALP activity expressed in LCPS is directly proportional to the level of ALP expressed by the cells. The half maximal effective concentrations of the test compounds (EC50) were calculated from the curves fitted to the concentration-response data with a four parameter logistic model in XLfit software version 2.0 (IDBS) or later.

The compounds of Examples 1-24 were tested in binding assay 1 and in the transactivation assays 1 and 2.

The compounds of Examples 1-24 exhibit one or more of the following:
(i) a binding affinity to the estrogen receptor α-subtype in the range of $IC_{50}$ 1 to 10,000 nM in binding assay 1;
(ii) a binding affinity to the estrogen receptor β-subtype in the range of $IC_{50}$ 1 to 10,000 nM in binding assay 1;
(iii) a potency in the range of $EC_{50}$ 1 to 10,000 nM at the estrogen receptor α-subtype in transactivation assay 1;
(iv) a potency in the range of $EC_{50}$ 1 to 10,000 nM at the estrogen receptor β-subtype in transactivation assay 2.

Preferred Example compounds of the invention are those which exhibit a binding affinity to the estrogen receptor β-subtype at lower concentrations within the $IC_{50}$ range shown above. For example, the compounds of Examples 1-3, 5-8, 10-12, 15-18 and 20-24 exhibit a binding affinity to the estrogen receptor β-subtype in the range of $IC_{50}$ 1 to 200 nM in binding assay 1.

Preferred Example compounds of the invention are those which are selective for the estrogen receptor β-subtype over the estrogen receptor β-subtype in binding assay 1. For example, the compounds of Examples 1-3 and 6-8, 10-12, 15-18 and 20-24 display selectivity for the estrogen receptor β-subtype of 50 or greater in the binding assay.

Preferred Example compounds of the invention are those which display a potency at the estrogen receptor β-subtype at lower concentrations within the $EC_{50}$ range shown above. For example, the compounds of Examples 1-13 and 15-24 exhibit a potency in the range of $EC_{50}$ 0.1 to 200 nM at the estrogen receptor β-subtype in transactivation assay 2, with the compounds of Examples 2-3, 5-8, 10-12 and 16-24 exhibiting a potency in the range of $EC_{50}$ 0.1 to 10 nM.

Preferred Example compounds of the invention are those which are selective for the estrogen receptor β-subtype over the estrogen receptor α-subtype in the transactivation assays 1 and 2. For example, the compounds of Examples 1-3 and 6, 8, 10-13, 15-20 and 22-24 display selectivity for the estrogen receptor β-subtype of 50 or greater in the transactivation assays.

The invention claimed is:
1. A compound of formula(I) or a pharmaceutically acceptable ester, amide, solvate or salt thereof, including a salt of such an ester or amide, and a solvate of such an ester, amide or salt,

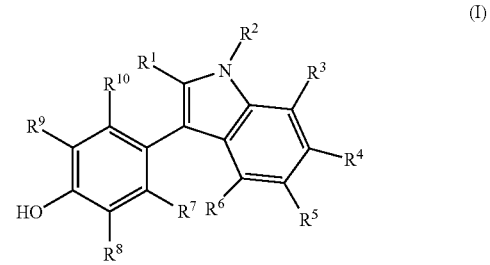

(I)

wherein $R^1$ is selected from the group consisting of halogen, cyano, nitro, $OR^A$, $N(R^B)_2$, —C(O)$C_{1-4}$alkyl, —SO$_2$C$_{1-4}$alkyl, C$_{1-6}$alkyl, C$_{2-6}$alkenyl, C$_{2-6}$alkynyl, haloC$_{1-6}$alkyl, dihaloC$_{1-6}$alkyl, trihaloC$_{1-6}$alkyl, haloC$_{2-6}$alkenyl, dihaloC$_{2-6}$alkenyl, trihaloC$_{2-6}$alkenyl, cyanoC$_{1-6}$alkyl, C$_{1-4}$alkoxyC$_{1-6}$ alkyl, C$_{3-8}$cycloalkyl, C$_{3-8}$cycloalkylC$_{1-6}$alkyl, phenyl, benzyl, and 5-10 membered heterocyclyl, wherein said phenyl, benzyl or heterocyclyl group can be either unsubstituted or substituted with from 1 to 3 substituents, each substituent being independently selected from the group consisting of $OR^A$, halogen, cyano, nitro, —C(O)C$_{1-4}$alkyl, C$_{1-6}$alkyl, C$_{2-6}$alkenyl, C$_{2-6}$alkynyl, haloC$_{1-6}$alkyl, dihaloC$_{1-6}$alkyl and trihaloC$_{1-6}$alkyl;

$R^2$ is selected from the group consisting of cyano, nitro, N(OH)$_2$, —CHO, —CH=N—OH, —C(O)C$_{1-4}$alkyl optionally substituted with from 1 to 3 halogens, —SO$_2$C$_{1-4}$alkyl, —C(O)NH—OH, —C(NH$_2$)=N—OH, —C(CO$_2$H)=N—OH, —C(NH$_2$)=NH, —C(NH$_2$)=N—NH$_2$, —NH—C(NH$_2$)=NH, —NH—C(O) NH$_2$, —N=C(—NH—CH$_2$CH$_2$—NH—), —S—CN, —S—C(NH$_2$)=NH, —S—C(NH$_2$)=N—OH, —CO$_2$H, —CH(OH) CO$_2$H, —C(O)N(R$^C$) $_2$, —SO$_2$C$_{1-6}$alkyl, SO$_2$N(R$^C$)$_2$, —C(O)—C (O)—NH$_2$, —CH$_2$NH—CONH$_2$, —SO$_2$OR$^C$, —C(O) CO$_2$H, —CH$_2$SO$_3$H and 5-10 membered heterocyclyl wherein said heterocyclyl group can be either unsubstituted or substituted with from 1 to 3 substituents each substituent being independently selected from the group consisting of $OR^A$, halogen, cyano, nitro, C$_{1-6}$alkyl, C$_{2-6}$alkenyl, C$_{2-6}$alkynyl, haloC$_{1-6}$alkyl, dihaloC$_{1-6}$alkyl and trihaloC$_{1-6}$alkyl;

each of $R^3$, $R^4$, $R^5$, $R^6$, $R^7$, $R^8$, $R^9$ and $R^{10}$ is independently selected from the group consisting of hydrogen, $OR^A$, halogen, cyano, nitro, C$_{1-6}$alkyl, C$_{2-6}$alkenyl, C$_{2-6}$alkynyl, haloC$_{1-6}$alkyl, dihaloC$_{1-6}$alkyl and trihaloC$_{1-6}$alkyl;

each $R^A$ is independently selected from the group consisting of hydrogen, C$_{1-6}$alkyl, C$_{2-6}$alkenyl, C$_{2-6}$alkynyl, C$_{3-8}$cycloalkyl, C$_{3-8}$cycloalkylC$_{1-6}$alkyl, phenyl, benzyl and 5-10 membered heterocyclyl, each optionally substituted by from 1 to 3 halogen atoms; and each $R^B$ is independently selected from the group consisting of hydrogen, $C_{1-6}$alkyl, $C_{2-6}$alkenyl, $C_{2-6}$alkynyl, $C_{3-8}$cycloalkyl, $C_{3-8}$cycloalkyl$C_{1-6}$alkyl, phenyl, benzyl and 5-10 membered heterocyclyl, each optionally substituted by from 1 to 3 halogen atoms; and each $R^C$ is independently selected from the group consisting of hydrogen and $C_{1-6}$alkyl.

2. A compound as claimed in claim 1, in which $R^2$ represents cyano, —CH=N—OH, —C(O)N($R^C$)$_2$, —C(NH$_2$)=N—OH, SO$_2$N($R^C$)$_2$, —SO$_2$C$_{1-6}$alkyl, —SO$_2$OR$^C$ or a 5-6 membered heterocyclyl group being either unsubstituted or substituted with from 1 to 3 substituents each substituent being independently selected from the group consisting of OR$^A$, halogen, cyano, nitro, $C_{1-6}$alkyl, $C_{2-6}$alkenyl, $C_{2-6}$alkynyl, halo$C_{1-6}$alkyl, dihalo$C_{1-6}$alkyl and trihalo$C_{1-6}$alkyl.

3. A compound as claimed in claim 2, in which $R^2$ represents —CH=N—OH or —C(O)NH$_2$.

4. A compound as claimed in claim 1, in which $R^1$ represents $C_{1-6}$alkyl, $C_{2-6}$alkenyl, $C_{2-6}$alkynyl, phenyl, or a 5-10 membered heterocyclyl, wherein said phenyl or heterocyclyl group can be either unsubstituted or substituted with from 1 to 2 substituents, each substituent being independently selected from cyano or $C_{1-6}$alkyl.

5. A compound as claimed in claim 4, in which $R^1$ represents phenyl or a 5-6 membered heterocyclyl, wherein said phenyl or heterocyclyl group is substituted with from 1 to 2 substituents, said substituent or substitutents being $C_{1-6}$alkyl.

6. A compound as claimed in claim 5, in which $R^1$ represents phenyl or a 5-membered heterocyclyl, wherein said phenyl or heterocyclyl group is substituted with 2 substituents, said substituents being methyl.

7. A compound as claimed in claim 6, in which $R^1$ represents 2,5-dimethylphenyl, 3,5-dimethylisoxazol-4-yl, 2,4-dimethyl-thien-3-yl, or 3,5-dimethylisothiazol-4-yl.

8. A compound as claimed in claim 1, in which each of $R^3$, $R^4$, $R^5$, $R^6$, $R^7$, $R^8$, $R^9$ and $R^{10}$ is independently selected from hydrogen and halogen.

9. A compound as claimed in claim 8, in which each of $R^3$, $R^4$, $R^5$, and $R^6$ represents hydrogen, and one or two of $R^7$, $R^8$, $R^9$ and $R^{10}$ represents fluorine and the remainder of $R^7$, $R^8$, $R^9$ and $R^{10}$ represent hydrogen.

10. A compound as claimed in claim 1, which is any one of the following compounds:

2-(3,5-dimethylisoxazol-4-yl)-3-(4-hydroxyphenyl)-1H-indole-1-carbonitrile;

2-(3,5-dimethylisoxazol-4-yl)-N'-hydroxy-3-(4-hydroxyphenyl)-1H-indole-1-carboximidamide;

2-(3,5-dimethylisoxazol-4-yl)-3-(4-hydroxyphenyl)-1H-indole-1-carboxamide;

2-(3,5-dimethylisoxazol-4-yl)-3-(4-hydroxyphenyl)-N,N-dimethyl-1H-indole-1-sulfonamide;

2-(3,5-dimethylisoxazol-4-yl)-3-(4-hydroxyphenyl)-1H-indole-1-carbaldehyde oxime;

4-(2-(3,5-dimethylisoxazol-4-yl)-1-(methylsulfonyl)-1H-indol-3-y1)phenol;

2-((Z)-but-2-en-2-yl)-N'-hydroxy-3-(4-hydroxyphenyl)-1H-indole -1-carboximidamide;

2-(3,5-dimethylisoxazol-4-yl)-N-ethyl-3-(4-hydroxyphenyl)-1H-indole-1-carboxamide;

2-(3,5-dimethylisoxazol-4-yl)-3-(4-hydroxyphenyl)-N-methyl-1H-indole-1-carboxamide;

2-(2,4-dimethylthiophen-3-yl)-N'-hydroxy-3-(4-hydroxyphenyl)-1H-indole-1-carboximidamide;

2-(2,4-dimethylthiophen-3-yl)-3-(4-hydroxyphenyl)-1H-indole-1-carboxamide;

2-(2,6-dimethylphenyl)-N'-hydroxy-3-(4-hydroxyphenyl)-1H-indole-1-carboximidamide;

2-(3,5-dimethylisoxazol-4-yl)-3-(4-hydroxyphenyl)-N-isopropyl-1H-indole-1-carboxamide;

2-(3,5-dimethylisoxazol-4-yl)-3-(4-hydroxyphenyl)-N-pentyl-1H-indole-1-carboxamide;

2-(2,4-dimethylthiophen-3-yl)-N-ethyl-3-(4-hydroxyphenyl)-1H-indole-1-carboxamide;

3-(3,5-difluoro-4-hydroxyphenyl)-2-(3,5-dimethylisoxazol-4-yl)-N'-hydroxy-1H-indole-1-carboximidamide;

3-(2,3-difluoro-4-hydroxyphenyl)-2-(3,5-dimethylisoxazol-4-yl)-N'-hydroxy-1H-indole-1-carboximidamide;

2-(3,5-dimethylisoxazol-4-yl)-3-(2-fluoro-4-hydroxyphenyl)-N'-hydroxy-1H-indole-1-carboximidamide;

3-(2,5-difluoro-4-hydroxyphenyl)-2-(3,5-dimethylisoxazol-4-yl)-N'-hydroxy-1H-indole-1-carboximidamide;

2-(3,5-dimethylisoxazol-4-yl)-3-(3-fluoro-4-hydroxyphenyl)-N'-hydroxy-1H-indole-1-carboximidamide;

5-chloro-2-(3,5-dimethylisoxazol-4-yl)-N'-hydroxy-3-(4-hydroxyphenyl)-1H-indole-1-carboximidamide;

2-(2,4-dimethylfuran-3-yl)-N'-hydroxy-3-(4-hydroxyphenyl)-1H-indole-1-carboximidamide;

2-(3,5-dimethylisothiazol-4-yl)-N'-hydroxy-3-(4-hydroxyphenyl)-1H-indole-1-carboximidamide;

2-(3,5-dimethylisothiazol-4-yl)-3-(4-hydroxyphenyl)-1H-indole-1-carboxamide;

5-chloro-2-(3,5-dimethylisoxazol-4-yl)-N'-hydroxy-3-(4-hydroxyphenyl)-1H-indole-1-carboximidamide;

2-(2,4-dimethylfuran-3-yl)-N'-hydroxy-3-(4-hydroxyphenyl)-1H-indole-1-carboximidamide;

2-(3,5-dimethylisothiazol-4-yl)-N'-hydroxy-3-(4-hydroxyphenyl)-1H-indole-1-carboximidamide;

2-(3,5-dimethylisothiazol-4-yl)-3-(4-hydroxyphenyl)-1H-indole-1-carboxamide;

or a pharmaceutically acceptable ester, amide, solvate or salt thereof, including a salt of such an ester or amide, and a solvate of such an ester, amide or salt thereof.

11. A pharmaceutical composition which comprises a compound as claimed in claim 1, together with a pharmaceutically acceptable carrier.

* * * * *